(12) United States Patent
Mansfield et al.

(10) Patent No.: US 9,719,888 B2
(45) Date of Patent: Aug. 1, 2017

(54) COTTON ACQUISITION AND TRACKING SYSTEM

(71) Applicant: Quantitative Engineering Solutions, LLC, Farragut, TN (US)

(72) Inventors: Joe Mansfield, Knoxville, TN (US); Ken Campbell, Farragut, TN (US); Clark A. Roberts, Maryville, TN (US)

(73) Assignee: Quantitative Engineering Solutions, LLC, Knoxville, TN (US)

( * ) Notice: Subject to any disclaimer, the term of this patent is extended or adjusted under 35 U.S.C. 154(b) by 656 days.

(21) Appl. No.: 14/048,635

(22) Filed: Oct. 8, 2013

(65) Prior Publication Data

US 2014/0096623 A1    Apr. 10, 2014

Related U.S. Application Data

(60) Provisional application No. 61/711,357, filed on Oct. 9, 2012.

(51) Int. Cl.

| G01N 1/04 | (2006.01) |
|---|---|
| G01N 1/08 | (2006.01) |
| G01N 33/36 | (2006.01) |
| G01N 35/02 | (2006.01) |
| G01N 35/04 | (2006.01) |

(52) U.S. Cl.
CPC ............... *G01N 1/04* (2013.01); *G01N 1/08* (2013.01); *G01N 33/362* (2013.01); *G01N 35/02* (2013.01); *G01N 2035/0484* (2013.01)

(58) Field of Classification Search
CPC    D01G 9/10; D01G 9/08; G01N 33/36; G01N 33/362; G01N 33/367

USPC .......................................................... 73/160
See application file for complete search history.

(56) References Cited

U.S. PATENT DOCUMENTS

| 2,582,219 | A | * | 1/1952 | Ardito | A47L 9/1427 |
| | | | | | 55/373 |
| 3,362,048 | A | * | 1/1968 | Hale | D01G 15/48 |
| | | | | | 19/106 A |
| 3,604,061 | A | * | 9/1971 | King, Jr. | D01G 15/763 |
| | | | | | 19/107 |
| 3,614,813 | A | * | 10/1971 | Sloan | D01G 15/763 |
| | | | | | 19/107 |
| 3,983,273 | A | * | 9/1976 | Elliott | D01G 15/26 |
| | | | | | 19/106 R |

(Continued)

*Primary Examiner* — R. A. Smith
*Assistant Examiner* — Herbert K Roberts
(74) *Attorney, Agent, or Firm* — Knox Patents; Thomas A. Kulaga

(57) ABSTRACT

Apparatus for a cotton sample acquisition and tracking system. The system includes a loading station in which a pair of primary sample halves are loaded in a carrier. The primary samples are identified and transported to a sub-sample station that extracts a sub-sample from the primary sample. The sub-samples are conditioned and transported to various testing stations. The primary samples are transported via a conveyor system. The sub-samples are transported through a pneumatic system. The sub-sample station advances the primary sample against a pick drum that pulls tufts from the primary sample. The tufts flow through a cotton containment system into an indexer that collects, conditions, and routes the tufts as a sub-sample. The sub-samples are staged in a carousel for continued conditioning and storage until the test equipment is ready to process the sub-sample.

12 Claims, 11 Drawing Sheets

(56) References Cited

U.S. PATENT DOCUMENTS

| | | | | |
|---|---|---|---|---|
| 4,100,651 A * | 7/1978 | Wornall | ............... | D01G 13/00 19/145.5 |
| 4,403,374 A * | 9/1983 | Wood | ............... | D04H 1/72 19/105 |
| 4,410,340 A * | 10/1983 | Wurmli | ............... | B01D 46/26 100/192 |
| 4,759,102 A * | 7/1988 | Verzilli | ............... | D01G 15/78 19/111 |
| 4,993,119 A * | 2/1991 | Roberson | ............... | D01G 13/00 19/105 |
| 5,367,747 A * | 11/1994 | Shofner | ............... | D01G 99/00 19/65 R |
| 5,872,440 A * | 2/1999 | Brabant | ............... | D01G 15/48 318/127 |
| 6,052,871 A * | 4/2000 | Patelli | ............... | D01G 15/785 15/256.53 |
| 6,098,454 A * | 8/2000 | Ghorashi | ............... | G01N 33/362 73/160 |
| 6,314,806 B1 * | 11/2001 | Ghorashi | ............... | G01N 33/362 19/66 CC |
| 2002/0029151 A1 * | 3/2002 | Shofner | ............... | D01G 31/006 705/1.1 |
| 2005/0034278 A1 * | 2/2005 | Trivedi | ............... | D01G 15/78 19/98 |

* cited by examiner

COTTON ACQUISITION AND TRACKING SYSTEM

CROSS-REFERENCE TO RELATED APPLICATIONS

This application claims the benefit of U.S. Provisional Application No. 61/711,357, filed Oct. 9, 2012.

STATEMENT REGARDING FEDERALLY SPONSORED RESEARCH OR DEVELOPMENT

Not Applicable

BACKGROUND

1. Field of Invention

This invention pertains to a cotton acquisition and tracking system. More particularly, this invention pertains to a system that receives a cotton sample, removes a sub-sample for testing while other sample testing is performed.

2. Description of the Related Art

The U.S. Department of Agriculture's (USDA) Agricultural Marketing Service (AMS) administers programs that facilitate the efficient, fair marketing of U.S. agricultural products, including food, fiber, and specialty crops. One of the programs of the Cotton and Tobacco Programs (C&T) is the Grading and Classing program for cotton. The Grading and Classing program for cotton classifies cotton samples taken from full bales at gin locations and transported to designated testing laboratories. The objective of the Grading and Classing program for cotton is to facilitate interstate and foreign commerce in cotton by providing official quality determinations that aid in marketing. The USDA AMS accomplishes this objective by inspecting, identifying, and certifying that product quality is in accordance with official standards. The program determines the quality of the current crop and of the annual carryover. Cotton standardization ensures uniformity in grading and classing.

Grading and classing cotton is a labor intensive operation conducted within a short time after the crop is picked. Samples are taken from full bales at gin locations. The samples are then transported to a testing laboratory. There, the sample is identified and tested. Testing is done with fiber testing instruments. The various tests includes determining the color grade and the leaf grade of American Upland Cotton, the grades of American Pima Cotton, the fiber length, Length Uniformity Index, fiber strength, Micronaire, trash, and color. High Volume Instruments (HVI) are used for the classification of all Upland and American Pima cotton. Additionally, trash and color are determined by HVI equipment.

The testing laboratories operate under strict climate requirements for cotton testing of 70 degrees F., plus or minus 1 degree and 65 percent relative humidity plus or minus 2 percent. The cotton fiber reacts to changes in moisture. Therefore, it is necessary to condition all samples to the testing laboratory environment prior to testing. It is common to use Rapid Conditioning Units (RCU) for active conditioning. The RCU is a mechanism that conveys trays of samples along an air plenum that has conditioned air that conditions the cotton quickly (usually in less than 15 minutes from start to finish). The samples then move to a laboratory where HVIs test the characteristics of fiber properties and the corresponding data is then made available for the cotton industry to use to market cotton worldwide. Each HVI has a cycle time, but depends upon an operator to manually retrieve the main cotton samples from plastic trays, pull three (3) sub-samples from each of those samples, and load those sub-samples into pre-determined locations on the HVI to test for fiber length, strength, uniformity, and Micronaire (fineness and maturity). In addition, the operator places the remainder of the main sample in a designated location on the HVI to test fiber color and trash content. These instruments are solely relied upon by USDA and the domestic and international cotton industries to provide accurate and timely classification data for the marketing stream. The test data is transmitted in real time, as samples are tested, to mainframe computers and made available to owners or agents of the cotton all over the world.

The USDA AMS is considered the world's leader in HVI testing and tests virtually every bale of cotton grown in the U.S. each year (approximately 15-18 million samples on average in a typical year). Speed, accuracy and efficiency are key components of the operation. The current system relies upon multiple operators to perform these tests. The human element, despite training and experience, is always susceptible to error and inefficiencies. For example, a human operator pulls multiple sub-samples from each primary sample. The sub-samples are susceptible to variations of size, location, transport and handling, and placement into the HVI equipment. These variations potentially effect the consistency and accuracy of the measurements.

BRIEF SUMMARY

According to one embodiment of the present invention, a cotton acquisition and tracking system is provided. The cotton acquisition and tracking system includes a series of stations connected by a conveyor. An initial loading station has a pair of primary cotton sample halves loaded into a two-compartment primary sample carrier. The identification of the primary sample is verified, as is the identification of the primary sample carrier. The conveyor moves the primary sample carrier to the sub-sampling station, where a sub-sample is collected from each primary sample half. The conveyor moves the primary sample carrier to test station two and then test station three where the primary sample is further processed after identification. In one embodiment, test station two is a color/trash station and test station three is a classer station.

At the sub-sampling station the primary sample is positioned at a sub-sampling mechanism that removes a quantity of fibers and transports them to an indexer where a sub-sample is collected and conditioned. From there the sub-sample moves to a staging device. In one embodiment, the fibers are removed from the primary sample by an extraction drum, with the fibers transported in a vacuum pneumatic system. In this way the sub-sample is collected with minimal fiber damage and with consistency between sub-samples.

During and after fiber removal and collection of the sub-sample, the sub-sample is conditioned with air at a selected temperature and with a selected relative humidity. After conditioning, the sub-sample is transferred to test station one, which can be a high volume instrument for testing cotton. In some cases the sub-sample is held in a staging area, such as a carousel, until the test station is ready to process the sub-sample. The sub-samples are transported through a vacuum pneumatic system. In this way the needs for conditioning are reduced over conventional use of a rapid conditioning unit (RCU), thereby reducing power requirements and sample preparation time.

BRIEF DESCRIPTION OF THE SEVERAL VIEWS OF THE DRAWINGS

The above-mentioned features will become more clearly understood from the following detailed description read together with the drawings in which.

DETAILED DESCRIPTION

Apparatus for a cotton acquisition and tracking system 100 is disclosed. Cotton samples 102 undergo multiple tests in an automated system 100. Various components and devices are generally indicated with a reference number and particular embodiments and variations are shown in the figures and described below have an alphabetic suffix, for example, the three-way valves are referred generically as item 714 and the individual valves are referenced as items 714-A, 714-B. Another example is the sub-sample staging device 108 that is depicted in two embodiments 108-A, 108-B.

Figure 1:
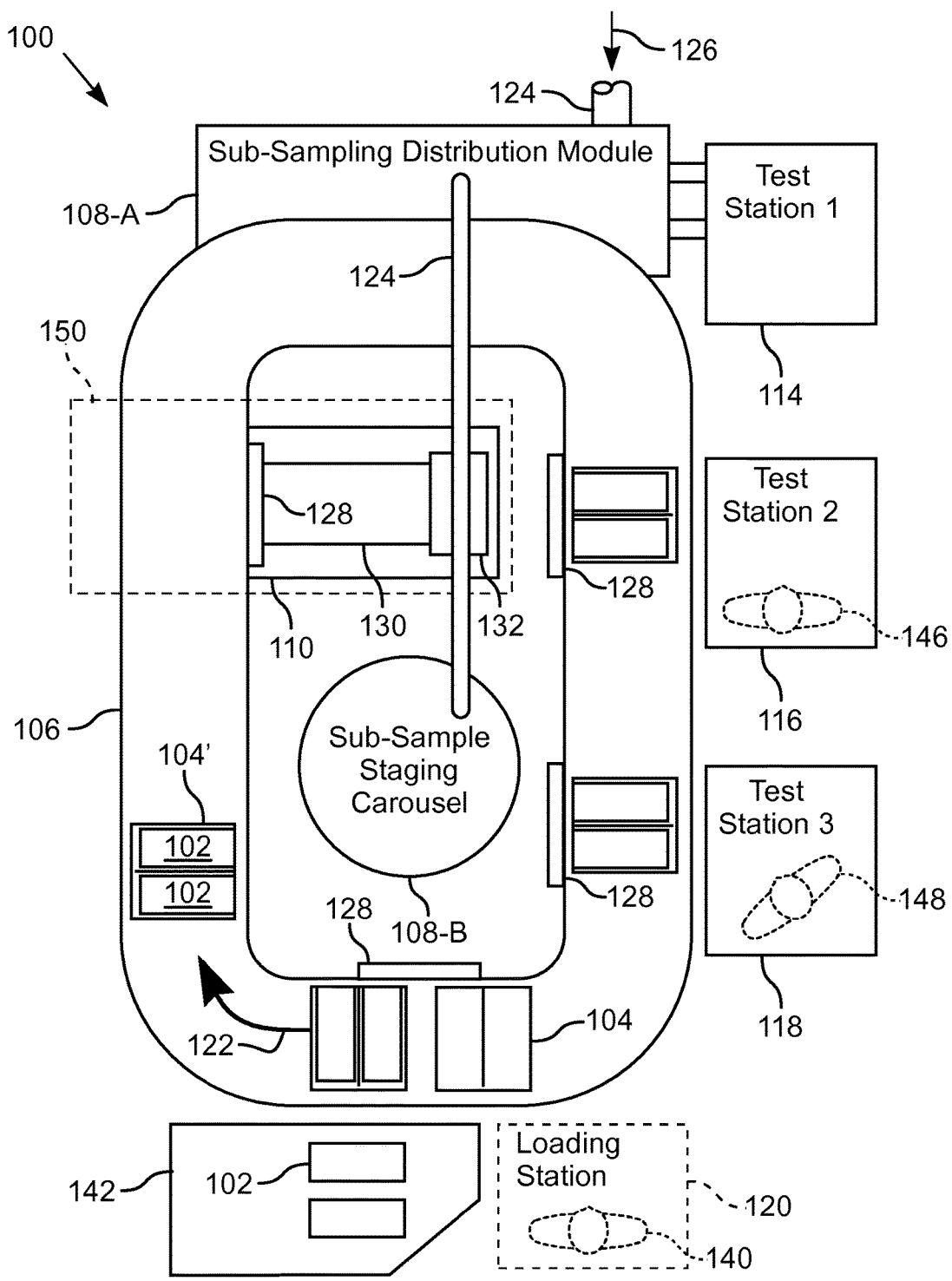
FIG. 1 is a plan view of one embodiment of a cotton acquisition and tracking system.

FIG. 1 illustrates a plan view of one embodiment of a cotton acquisition and tracking system 100. The system 100 includes a conveyor 106 that loops between the various stations 120, 150, 116, 118. The illustrated embodiment of the sampling system 100 shows only a single one of each of the various stations 120, 150, 116, 118. Other embodiments have multiple stations 120, 150, 116, 118. For example, with a 24 second cycle time for a single primary sample 102, the sampling system 100 can accommodate six test stations one 114, where test station one 114 is a cotton testing instrument such as a high volume instrument. That is, the system 100 is scalable to accommodate multiple test stations, depending upon the throughput of the sub-sampler station 150.

In the illustrated embodiment, at the loading station 120 is a table 142 that holds the cotton samples 102 to be tested. In other embodiments the table 142 is instead a conveyor that transports the samples 102 to the loading station 120. A production assistant (PA) 140 mans the loading station 120. The production assistant 140 prepares the samples 102 by placing a pair of sample halves 102 into a primary sample carrier (PSC) 104 on the conveyor 106. That is, a sample 102 from a single bale is divided into halves, which are processed as a pair. In one embodiment, the production assistant 140 manually scans the bale identification tag of the sample 102 associated with a bale that is loaded into a primary sample carrier 104'. In one such embodiment, the bale tag identifier is written to an radio frequency identity (RFID) tag 406 associated with a primary sample carrier 104, 104'. In another embodiment, the loaded primary sample carrier 104' passes by a scanner 128 near the loading station 120.

In another embodiment of the loading station 120, the operation is automated. The production assistant 40 loads the primary sample halves 102 directly to a tabulated indexing belt conveyor, which moves and positions the two half-samples 102 and associated bale tag 402, 404 at an Auto-Loading station. The two halves of the sample 102 are then automatically transferred to the primary sample carrier 104 and the bale tag information is recorded to the identifiers on the primary sample carrier 104. As the primary samples are moved to the primary sample carrier 104, a Load Assist mechanism deploys to insure the samples are constrained within the primary sample carrier 104 during loading. The primary sample carrier 104 moves to and is then processed by the sub-sampler.

In another embodiment, the primary sample is loaded by the production assistant 40 directly to a tabulated indexing belt conveyor, which moves and positions the two half-samples 102 and associated identifying bale tag 402, 404 at an Imaging System. The cameras automatically move into position above and below each half of the primary sample carrier 104 to capture two images of each half of the primary sample 102, and capture and store the bale tag information. Once the imaging is complete, the primary sample 102 moves to the Auto-Loading station described above. The bale tag information captured by the Imaging System is then transferred to the primary sample carrier identifying tags 402, 404.

In yet another embodiment, the primary sample 102 moves directly to the sub-sampler 150, such as through a fixed chute or other assembly that maintains traceability of the primary sample 102. In such an embodiment, the conveyor 106 and primary sample carrier 104 are not necessary for transporting the primary sample 102 from the loading station 120 to the sub-sampler 150.

The conveyor 106 moves in a direction 122 to transport the loaded primary sample carrier 104' to the sub-sampler station 150. A scanner 128 at the sub-sampler station 150 identifies the loaded primary sample carrier 104'. The conveyor 106 then transports the loaded primary sample carrier 104' to the color/trash station 116 for the person 146 manning test station two 116. A scanner 128 at test station two 116 identifies the loaded primary sample carrier 104'. The conveyor 106 then transports the loaded primary sample carrier 104' to test station three 118. A scanner 128 at test station three 118 identifies the loaded primary sample carrier 104' for the person 148 manning test station three 118. At test station three 118 the samples 102 are removed from the primary sample carrier 104 and the empty primary sample carrier 104 returns to the loading station 120 for the next sample 102 to be inserted.

The sub-sampler station 150 includes a sub-sampler module 110. In the illustrated embodiment, a second conveyor 130 moves a loaded primary sample carrier 104' to the sub-sampling mechanism 132. The sub-sampler mechanism 132 extracts a sub-sample 102-SS from the sample 102. FIG. 1 illustrates two alternative embodiments for handling the sub-samples 102-SS. The first embodiment includes moving the sub-sample 102-SS from the sub-sampler mechanism 132 to the sub-sampling distribution module 108-A, where the sub-samples 102-SS are staged until they are moved to test station one 114, where the sub-samples 102-SS are tested, such as with a high volume instrument (HVI). In this embodiment, the sub-samples 102-SS are temporarily held in a carrier, which is two plates with a sub-sample carrier 802 sandwiched therebetween. The sub-sampling distribution module 108-A receives conditioned air 126 through an inlet port 124. The conditioned air 126 is routed to the sub-sampler module 110. The conditioned air 126 is suitable for conditioning the sub-sample for testing.

In the other embodiment, the sub-sample 102-SS from the sub-sampler 132 is moved through the pneumatic system 124 to the sub-sample staging carousel 108-B, where the sub-samples 102-SS are stored in a conditioned environment until the sub-samples 102-SS are moved through the pneumatic system 124 to test station one 114, where the sub-samples 102-SS are tested.

Figure 2:
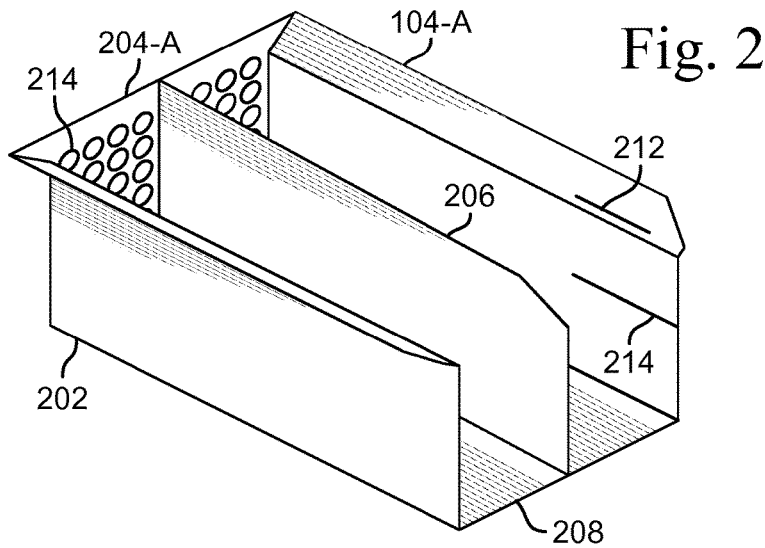
FIG. 2 is a perspective view of one embodiment of a primary sample carrier.
Figure 3:
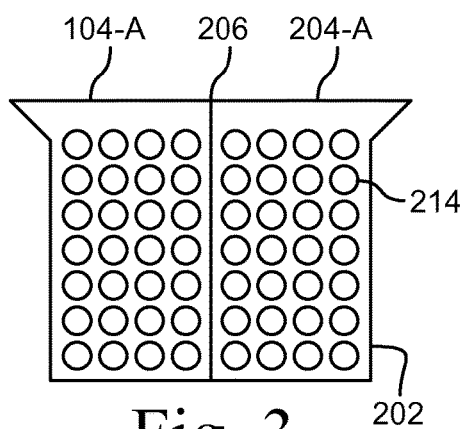
FIG. 3 is a front view of the embodiment of the primary sample carrier shown in FIG. 2.
Figure 4:
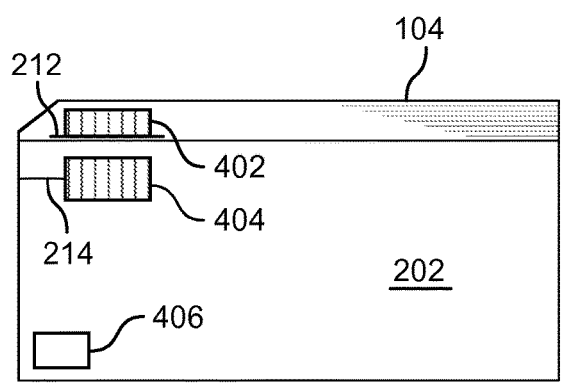
FIG. 4 is a left side view of the embodiment of the primary sample carrier shown in FIG. 2.

FIG. 2 illustrates a perspective view of one embodiment of a primary sample carrier 104-A. FIG. 3 illustrates a front view of the embodiment of the primary sample carrier 104-A shown in FIG. 2. FIG. 4 illustrates a left side view of a primary sample carrier 104.

The primary sample carrier 104 is a box-like structure that has a pair of sidewalls 202, a base 208, a divider 206, and a rear plate, or sub-sampling plate 204. Each sidewall 202, the divider 206, the base 208, and sub-sampling plate or wall 204 define a space dimensioned to receive one half of the pair of primary samples 102. The upper portion of the sidewalls 202 are angled away from the interior to aid in the insertion of the primary sample 102.

The rear of the primary sample carrier 104 is a sub-sampling plate 204. In the embodiment illustrated in FIGS. 2 and 3, the sub-sampling plate or wall 204-A has a series of openings or holes 214 through which a portion of the primary sample 102 protrudes when the sample 102 is pushed against the sub-sampling plate 204-A.

The illustrated embodiment of the primary sample carrier 104 is configured to have a permanent identifier 402 and a holder for a bale tag 404. The identifiers and tags 402, 404 are read by the scanners 128. A pair of permanent identifiers 402 are attached to the carrier 104 at the upper portion of each sidewall 202. The placement of the permanent identifiers 402 on the underside of the angled upper portion of the sidewalls 202 provides protection of the permanent identifiers 402 as the primary sample carriers 104 move on the conveyor 106. In this way, the likelihood of damaging the identifiers 402 is reduced. In the illustrated embodiment, a pair of identifiers 402 are provided for redundancy in case one identifier 402 is damaged such that the identification code on one identifier 402 cannot be read.

In the illustrated embodiment, a bale tag 404 corresponding to the primary sample 102 carried in the carrier 104 is attached to one sidewall 202. In one such embodiment, the bale tag 404 is inserted through a slot 212 in the canted portion of the sidewall 202 and into a holder on the outside of the sidewall 202. In another such embodiment, a second slot 214 in the sidewall is positioned to allow automatic extraction of the bale tag 404.

In one embodiment, the identifiers and tag 402, 404 are tags with bar codes that are read by bar code readers in the scanners 128. In other embodiments, either the permanent identifiers 402 or separate tags 406 are radio frequency identity (RFID) tags or other type of re-writable, machine readable tags. In such an embodiment, the RFID tags 402, 406 are written with a code associated with the identification code of the bale tag 404. The bale tag 404 is then placed in the carrier 104 with the primary sample 102. The scanners 128 read the RFID tag 402, 406 to identify the specific primary sample 102 in the carrier 104.

Figure 5:
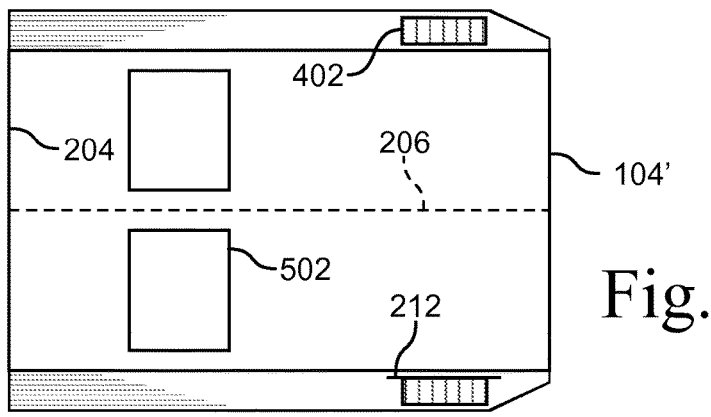
FIG. 5 is a bottom view of one embodiment of a primary sample carrier.

FIG. 5 illustrates a bottom view of another embodiment of a primary sample carrier 104'. The carrier 104' has a pair of windows 502 in the bottom 208. The windows 502 provide a view of the primary sample 102 in the carrier 104' for imaging, such as is performed at a color/trash station, such as test station two 116. In another embodiment, an automated imaging system uses the windows 502 to capture an image of the bottom of the sample 102 in the carrier 104'. The top of the carrier 104' is open, thereby allowing an image of the top of the sample 102 to also be captured.

Figure 6:
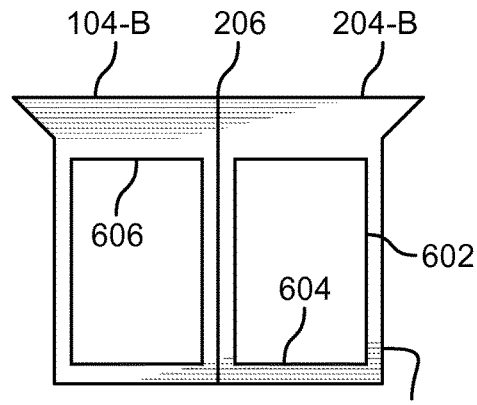
FIG. 6 is a front view of another embodiment of the primary sample carrier.

FIG. 6 illustrates a front view of another embodiment of the primary sample carrier 104-B. In the illustrated embodiment, the back wall 204-B includes a pair of windows 602. Each half of the cotton sample 102 has its own window 602. In this way, a sub-sample 102-SS is obtainable from each half of the cotton sample 102.

Each window 602 has a lower edge 604 and an upper edge 606. The lower edge 604 is elevated relative to the base 208. In this way, when the extraction drum 702 is rotating in a direction that is forcing the sample 102 toward the lower edge 602, the sample is restrained from being drawn out of the primary sample carrier 104-B. The motion of the drum 702 relative to the sample 102 forces the sample 102 toward the base 208 and sample 102 catches or is restrained at the portion of the back wall 204-B between the base 208 and the lower edge 604 of the window 602. The height of the window 602 is dimensioned such that the back wall 204-B above the upper edge 606 restrains the sample 102 when the motion of the drum 702 relative to the sample 102 forces the sample 102 away from the base 208.

Figure 7:
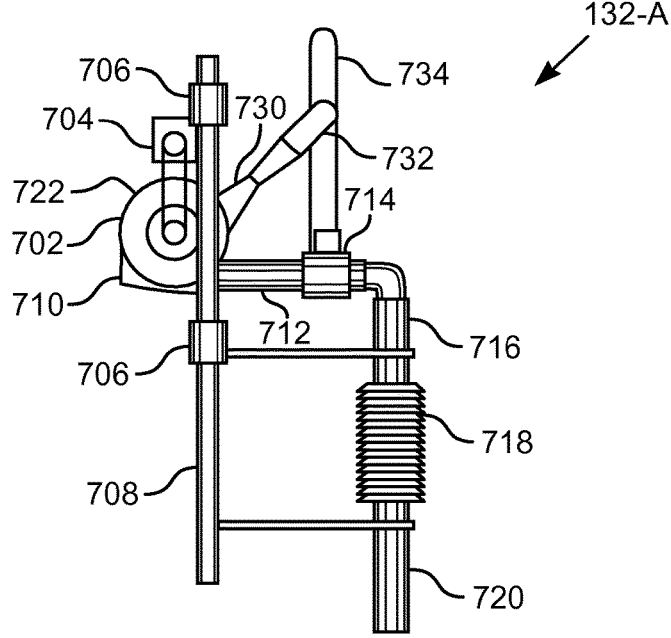
FIG. 7 is a side view of one embodiment of a sub-sampler mechanism.

FIG. 7 illustrates a side view of one embodiment of a sub-sampler mechanism 132-A. Because the primary sample carrier 104 carries a pair of cotton sample halves 102, the sub-sampler mechanism 132-A includes a pair of drums 702, one for each one of the pair of sample halves 102. In one embodiment, the sub-sampler mechanism 132-A has the capability of processing two loaded primary sample carriers 104' to produce two pairs of sub-samples 102-SS at one time.

The illustrated embodiment of the sub-sampler mechanism 132-A includes an extraction drum 702 that moves vertically to engage the sample 102 protruding from the sub-sampling plate 204-A. The extraction drum 702 rotates reciprocally by a motor 704. The extraction drum 702 also moves vertically along the vertical supports 704 such that the extraction drum 702 engages the full height of the sub-sampling plate 204-A. Sleeve bearings 706 maintain alignment of the extraction drum 702 with the sub-sampling plate 204-A such that the card pucks 722 on the extraction drum 702 engage the portion of the primary sample 102 protruding from the openings 214 in the sub-sampling plate 204-A. In another embodiment, the sub-sampler mechanism 132-A is stationary and the extraction drum 702 engages the primary sample 102 through the windows 602 in the sub-sampling plate 204-B of the primary sample carrier 104-B.

Figure 10:
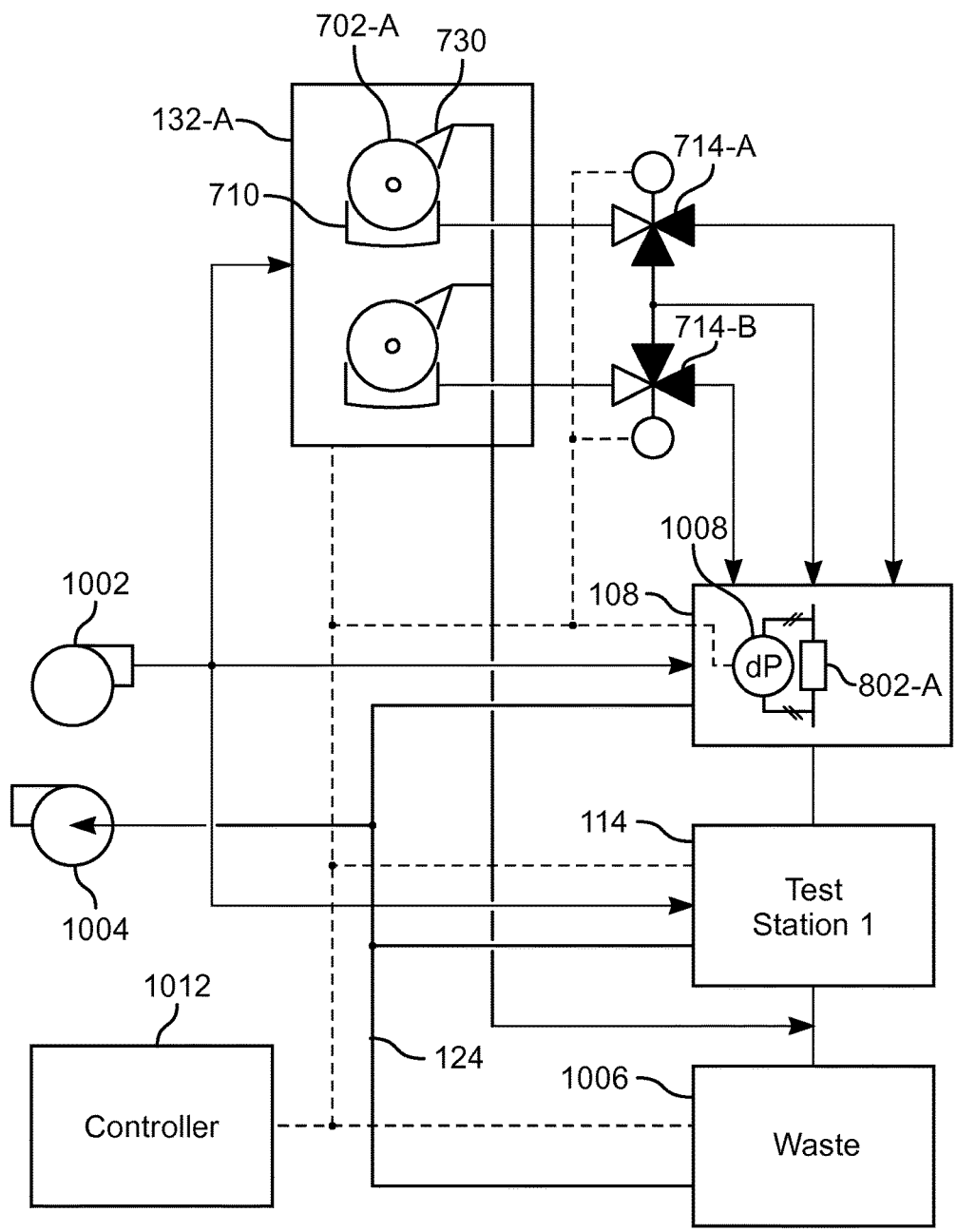
FIG. 10 is a simplified piping and instrumentation diagram of a sampling system with the embodiment of the sub-sampling mechanism shown in FIG. 7.

Under the extraction drum 702 is a shroud or vacuum nozzle 710 connected to a vacuum pipe or line 712. The vacuum line 712 is connected to a three-way valve 714 that is also connected to a second pipe 716 that is connected to a bellows 718. The bellows 718 allows for the shroud 710, the vacuum line 712, the valve 714, and the second pipe 716 to move vertically with the extraction drum 702 while the sample discharge pipe 720 remains stationary. The bellows 718 maintains the air-tightness of the pneumatic system 124 as the extraction drum 702 moves during the sub-sample collection. As seen in FIG. 10, the third connection to the three-way valve 714 is connected to a tee 722 that connects the three-way valves 714 associated with each of the pair of extraction drums 702 associated with each one of the pair of primary samples 102 in the carrier 104. The tee is connected to another second pipe 716 that is connected to another bellows 718 connected to another discharge pipe 720. In this way, a sub-sample 102-SS can be collected from each of the pair of primary samples 102 or, alternatively, a single sub-sample 102-SS can be collected from fibers of the pair of primary samples 102. In another embodiment, only one sample 102-SS is collected from each extraction drum 702 and the third connection is not needed.

After the required amount of fibers are removed and sent to the sub-sample carrier 802, all the fibers on the card cylinder must be removed to avoid contaminating other sub-samples 102-SS. A doffer 730 engages the extraction drum 702 to clean any remaining fibers from the puck 722 on the extraction drum 702. The doffer 730 is connected to a manifold 732 that is connected to a vacuum line 734 that carries the unneeded removed fibers for disposal.

The sub-sampler mechanism 132-A collects sub-samples by moving the puck 722 against the primary sample 102. The fibers removed from the primary sample 102 are doffed from the puck 722 and collected in the shroud 710 where they are transported through the vacuum line 712. In one embodiment, air jets directed toward the puck 722 assist in removing the fibers from the extraction drum 702. Depending upon the position of the three-way valve 714, the fibers are either pulled through the sub-sample discharge pipe 720-A or combined with the fibers from the other one of the pair of the primary sample as they are pulled through the sub-sample discharge pipe 720.

Figure 8:
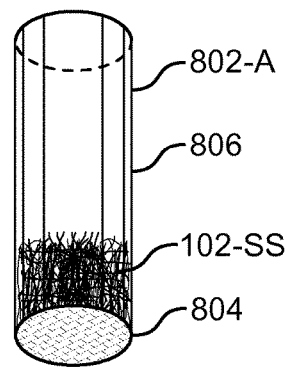
FIG. 8 is a perspective view of one embodiment of a sub-sample carrier.

FIG. 8 illustrates a perspective view of one embodiment of a sub-sample carrier 802-A. The sub-sample carrier 802-A is configured to be positioned in the flow stream of the vacuum pneumatic system 124. For example, the sub-sample carrier 802-A is mounted in a carrier between two plates with the carrier positionable so that each sub-sample 102-SS can be captured in a specific one of a sub-sample carrier 802-A. For example, the staging carrier 108-B includes a plurality of sub-sample carriers 802-A for storing sub-samples 102-SS before testing. In this way the flow of sub-samples 102-SS accommodates the vagaries of the sub-sampler 150 and the test station 114 to ensure a steady supply of sub-samples 102-SS to maximize efficiency of the test station 114.

The sub-sample carrier 802-A includes a hollow cylinder or tube 806 with one end having a fine mesh screen 804. In one embodiment, the hollow cylinder 806 is an acrylic tube. The fibers are pulled through the pneumatic system 124 and deposited into the sub-sample carrier 802-A against the screen 804 at the bottom of the tube 806. The sub-sample 102-SS is formed from the collected fibers.

The weight of the fibers making up the sub-sample 102-SS is determined with the sub-sample 102-SS in the sub-sample carrier 802-A. In one embodiment, the differential pressure is measured across the sub-sample 102-SS collected at the screen 804. The differential pressure across the sub-sample 102-SS correlates to the weight of the sub-sample 102-SS, which is desired to be between 8 and 15 grams.

Figure 9:
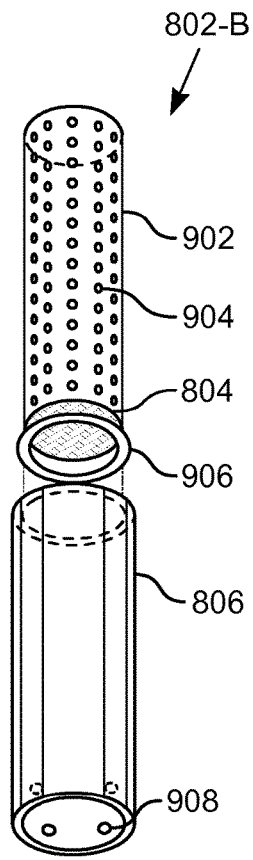
FIG. 9 is a perspective view of another embodiment of a sub-sample carrier.

FIG. 9 illustrates a perspective view of another embodiment of a sub-sample carrier 802-B. The sub-sample carrier 802-B is a vortex accumulation chamber that is configured to be positioned in the flow stream of the vacuum pneumatic system 124. For example, a plurality of sub-sample carriers 802-B are mounted in the carousel 108-B so that each sub-sample 102-SS can be captured in a specific one of a sub-sample carrier 802-A. In another embodiment the sub-sample carriers 802-B are included in an indexer 1312 that collects and conditions sub-samples 102-SS before moving them to a staging device like the carousel 108-B. The double-walled configuration of the carrier 802-B facilitates the flow of conditioned air through the fibers, thereby aiding conditioning of the collected sub-sample 102-SS within a short time period.

The sub-sample carrier 802-B includes an outer hollow cylinder or tube 806. The carrier 802-B also includes an inner hollow cylinder 902 with one end having a fine mesh screen 804. The sides of the inner hollow cylinder 902 have a series of openings 904 spaced along the cylindrical surface. The inner hollow cylinder 902 is held in fixed relation to the outer hollow cylinder 806. In one embodiment, the two cylinders 806, 902 are positioned between two plates with coaxial openings.

In one embodiment, the two cylinders 806, 902 are acrylic tubes. In operation, a vacuum from the pneumatic system 124 is applied to the screen 804 and the open end of the outer hollow cylinder 806 that is proximate the screen 804. In this way, air enters the end of the inner hollow cylinder 902 opposite the mesh 804. The air flows through the multitude of openings 904 and the mesh 804, thereby depositing or trapping the fibers from the sub-sampler mechanism 132 against the inner sidewall of the inner hollow cylinder 902 and against the screen 804 at the bottom of the tube 902. The sub-sample 102-SS is formed from the collected fibers.

The weight of the fibers making up the sub-sample 102-SS is determined with the sub-sample 102-SS in the sub-sample carrier 802-B. In one embodiment, the height of the fibers in the inner hollow cylinder 902 is measured, such as with an optical sensor 1304. The height of the fibers in the tube 902 correlates to the weight of the sub-sample 102-SS, which is desired to be between 8 and 15 grams.

A circular valve 906 is positioned adjacent the mesh 804. The valve 906 is a one-way valve that permits air to flow from the space between the two cylinders 806, 902 out the bottom of the sub-sample carrier 802-B and prevents air from flowing from the bottom of the carrier 802-B into the space between the two cylinders 806, 902. In this way the flow of conditioning air is facilitated during the storage phase, and, during the sub-sample extraction phase the extraction of the sub-sample is facilitated by directing the positive air pressure only through the inner cylinder 902. In various embodiments, the valve 906 is a reed-type valve or a flapper-type valve that permits air flow in only one direction. In the illustrated embodiment, the valve 906 is a ring of flexible sheet-like material. The valve 906 has a central opening to accommodate the mesh 804. The outer cylinder 806 has a plurality of nubs 908 on the inside surface that are positioned adjacent the bottom of the inside cylinder 902. The valve 906 is positioned at the bottom of the inside cylinder 902 adjacent the mesh 804, and the upper surface of the valve 906 is proximate the bottom surface of the nubs 908. In this way air flow through the valve 906 and the area between the two cylinders 806, 902 is permitted in the direction toward the mesh through the cylinders 806, 902, but is inhibited in the opposite direction. In this way a puff of air to discharge the sub-sample 102-SS from the carrier 802-B is limited to entering only the inner cylinder 902 of the carrier 802-B at the mesh 804. In one such embodiment, the nubs 908 also serve to secure the inner cylinder 902 inside the outer cylinder 806.

FIG. 10 illustrates a simplified piping and instrumentation diagram of a sampling system 100 with one embodiment sub-sampling mechanism 132-A. The pneumatic system 124 includes an air pump 1002 that supplies conditioned air to the sub-sampling mechanism 132-A, the sub-sample staging device 108-A, 108-B, and test station one 114. The conditioned air from the air pump 1002 is directed toward the portion of the system 100 where the sub-sample 102-SS passes. The air is conditioned to maintain a specified temperature and relative humidity to condition the sub-samples 102-SS.

The pneumatic system 124 also includes a vacuum pump 1004 connected to the sub-sample staging device 108-A, 108-B, test station one 114, and the waste device 1006. The vacuum pump 1004 is selectively connected to various pipes and equipment to pull the fibers or the sub-sample 102-SS from one location to another within the pneumatic system 124. For example, the vacuum from the vacuum pump 1004 is used to pull the fibers from the extraction drum 702-A, through the three-way valve 714-A, and to the staging device 108, where the sub-sample 102-SS is held until test station one 114 is ready to test the sub-sample 102-SS.

A controller 1012 is connected to the three-way valves 714, the sub-sampling staging device 108, which may include an indexer-type device 1312, test station one 114, and the waste device 1006. The differential pressure sensor 1008 is connected across a sub-sample carrier 802-A to determine if the sub-sample 102-SS is within weight limits. The controller 1012 monitors the measured differential pressure sensor 1008 and controls the sub-sampling mechanism 132-A and three-way valves 714 to collect more fibers until the desired volume or mass of the sub-sample 102-SS is obtained. In another embodiment the sensor 1008 is an optical sensor that detects a quantity of fibers in the carrier 802-A. In another embodiment, the sub-sample carrier 802-B is of the double-walled configuration, which provides enhanced conditioning capabilities, thereby shortening the conditioning time. The controller 1012 monitors test station one 114 and initiates the removal of a tested sub-sample 102-SS and the transfer of the next sub-sample 102-SS to be tested from the staging device 108. For example, the controller 1012 operates various valves in the pneumatic system 124 to pull the desired sub-sample 102-SS from the staging device 108 to test station one 114.

In one embodiment, the controller 1012 monitors the waste device 1006 to determine if the discarded sub-samples 102-SS need to be removed from the waste device 1006.

As used herein, the controller 1012 should be broadly construed to mean any device that accepts inputs and provides outputs based on the inputs, for example an analog control device or a computer or component thereof that executes software. In various embodiments, the controller 1012 is one of a specialized device or a computer for implementing the functions of the invention. The controller 1012 includes input/output (I/O) units for communicating with external devices and a processing unit that varies the output based on one or more input values. A computer-based controller 1012 includes a memory medium that stores software and data and a processing unit that executes the software. Those skilled in the art will recognize that the memory medium associated with the computer-based controller 1012 can be either internal or external to the processing unit of the processor without departing from the scope and spirit of the present invention.

The input component of the controller 1012 receives input from external devices, such as the differential pressure sensor 1008 and valve position sensors. The output component sends output to external devices, such as the three-way valves 112. The storage component stores data and program code. In one embodiment, the storage component includes random access memory and/or non-volatile memory.

The simplified piping and instrumentation diagram does not illustrate various connections and routings, however, those skilled in the art will recognize the need for such connections and routings and understand how to make such connections and routings, based on the components ultimately selected for use.

Figure 11:
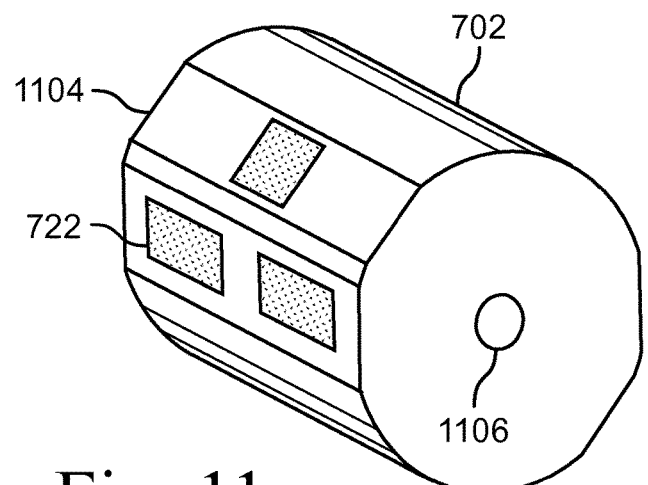
FIG. 11 is a perspective view of one embodiment of an extraction drum.
Figure 12:
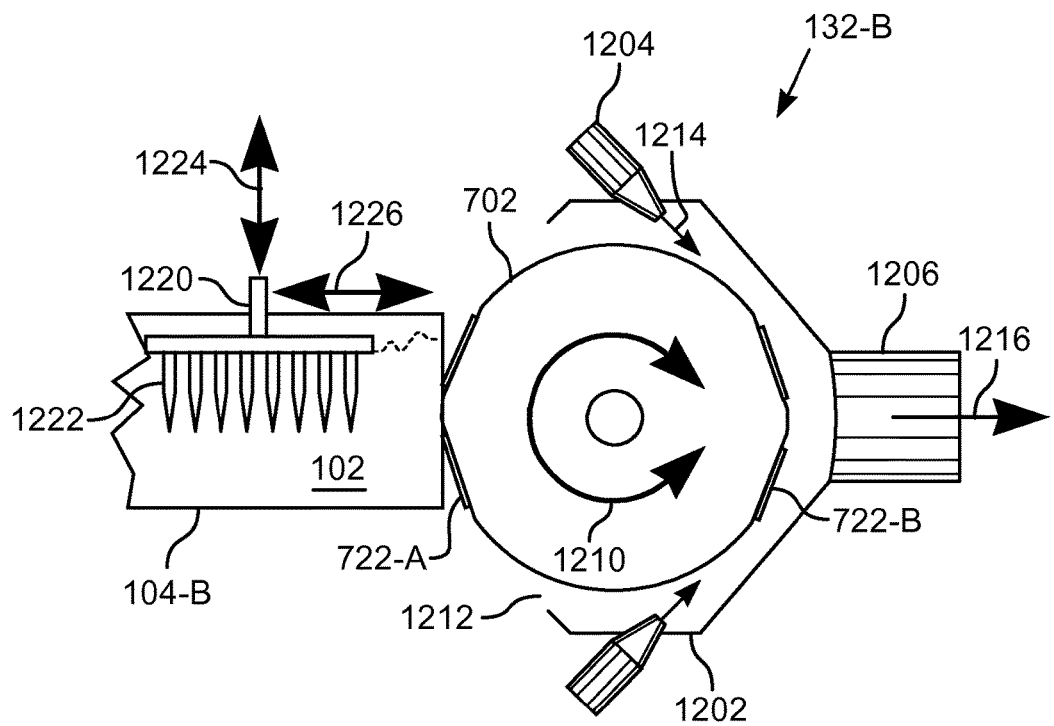
FIG. 12 is a symbolic side view of another embodiment of a sub-sampler mechanism showing the sample feed mechanism.

FIG. 11 illustrates a perspective view of one embodiment of an extraction drum 702. FIG. 12 illustrates a side view of another embodiment of a sub-sampler mechanism 132-B showing the sample feed mechanism 1220 The sub-sampler mechanism 132-B includes the extraction drum 702, the jets 1204, and the shroud 1202. The drum 702 is a cylinder that rotates 1210 about an axle 1106. The drum 702 is dimensioned to engage the window 602 in the primary sample carrier 104-B. Because the primary sample carrier 104-B has two windows 602, two drums 702 are positioned in tandem, side-by-side. Illustrated adjacent the drum 702 is a primary sample carrier 104-B holding a sample 102 that is engaged by a sample feed mechanism 1220 that moves in two axes 1224, 1226.

The sample feed mechanism 1220 includes a grid of picks 1222, which are needle-like protrusions configured to penetrate and grip the sample 102. The sample feed mechanism 1220 moves in two axes 1224, 1226. The first axis 1224 is perpendicular to the bottom of the primary sample carrier 104. The primary sample 102 defines a plane that is parallel to the bottom of the primary sample carrier 104 carrying that sample 102 and parallel to the axis of rotation 1210 of the drum 702. The second axis 1226 is parallel to the bottom of the primary sample carrier 104 and perpendicular to the axis of rotation 1210 of the drum 702.

In operation, the primary sample carrier 104 is moved toward the drum 702 with the pucks 722 engaging the sample 102 through the windows 602. The sample feed mechanism 1220 is positioned toward the end of the primary sample carrier 104 away from the windows 602. The feed mechanism 1220 is then lowered 1224 so that the picks 1222 engage the sample 102 securely. The feed mechanism 1220 moves in a direct 1226 toward the drum 722, thereby causing the sample 102 to engage the drum 722 through the window 602. The feed rate of the sample 102 is dependent upon the speed of the feed mechanism 1220 along the second axis 1226. When the feed mechanism 1220 reaches the end of its travel, which is near the windows 602, the feed mechanism 1220 moves upward 1224 and, when the picks 1222 clear the sample 102, backwards 1226 away from the windows 602. The feed mechanism 1220 re-engages the sample 102 when the mechanism 1220 is positioned toward the end of the primary sample carrier 104 away from the windows 602.

On opposite sides of the drum 702 are two pairs of flat sections 1104. Card pucks 722 are spaced apart on the flat sections 1104. In the illustrated embodiment, one flat section 1104 has two pucks 722 spaced apart and the other flat section 1104 has a puck 722 centered between the other two pucks 722. The card wire on the pucks 722 are aligned such that the pucks 722 grab fibers from primary sample 102 when the drum 702 rotates 1210 and moves the pucks 722 across the primary sample 102. The card wire on the pucks 722-B on the opposite side of the drum 702 are aligned in the opposite direction so that the pucks 722-B grab fibers when the drum rotates 1210 in the opposite direction.

On the side of the drum 702 opposite where the primary sample 102 is positioned is the shroud 1202. The shroud 1202 encloses a portion of the drum 702 and includes an outlet 1206 through which the extracted fibers flow 1216. The pneumatic system 124 applies a vacuum to the shroud outlet 1206, causing air to flow from the gaps 1212 between the open end of the shroud 1202 and the drum 702. In addition, a plurality of jets 1204 are positioned above and below the drum 702. The jets 1204 direct air 1214 tangentially to the drum 702 to blow the fibers extracted by the pucks 722 when the pucks 722 rotate past the air stream 1214 from the jets 1204. The air flowing through the gap 1212 and the air stream 1214 from the jets 1204 dislodges the fibers from the pucks 722 and carries the fibers through the shroud 1202 and into the outlet 1206. The fibers pass through the pneumatic system 124 until the fibers reach the sub-sample carrier 802, where the fibers are collected as a sub-sample 102-SS.

In the illustrated embodiment, the drum 702 rotates with a reciprocal motion 1210. The reciprocal motion 1210 allows one set of pucks 722-A to extract fibers from the primary sample 102 when the pucks 722-A rotate past the primary sample 102. As the pucks 722-A rotate past the jets 1204, the air stream 1214 from the jets 1204 blows the fibers off the pucks 722-A. The air stream from jets 1204 is timed to the rotation of the drum 702 to strike the pucks 722-A as puffs of air sufficient to dislodge the fibers from the card wire on the pucks 722-A. The drum 702 includes timing marks that trigger the puffs of air from the jets 1204. In this way the air jets serve to dislodge fibers without blowing the fibers around the drum 702 and out the opposite gap 1212. That is, the air stream from the jets 1204 are timed synchronously with the radial location of the pucks 722 relative to the extraction manifold or shroud 1202 and outlet 1206. After the pucks 722-A pass through the air stream 1214, the drum 702 changes direction 1210. When the pucks 722-A move across the primary sample 102 as the pucks 722-A return to their starting position, any remaining fibers on the pucks 722-A is removed by the rubbing of the primary sample 102 against the pucks 722-A. Upon reaching the starting position, the drum 702 changes direction 1210, again.

The pucks 722-B on the opposite side of the drum 702 operate in a similar manner, but 180 degrees out of phase with the other set of pucks 722-A. That is, when the drum 702 is rotated for the first set of pucks 722-A to extract fibers from the primary sample 102, the opposite set of pucks 722-B will move across the primary sample 102 so that the remaining fibers are removed from the pucks 722-B. With the pucks 722-A, 722-B oriented to extract and remove fibers as the drum 702 reciprocates in both directions 1210, the efficiency of the sub-sampling mechanism 132-B is increased.

Figure 13:
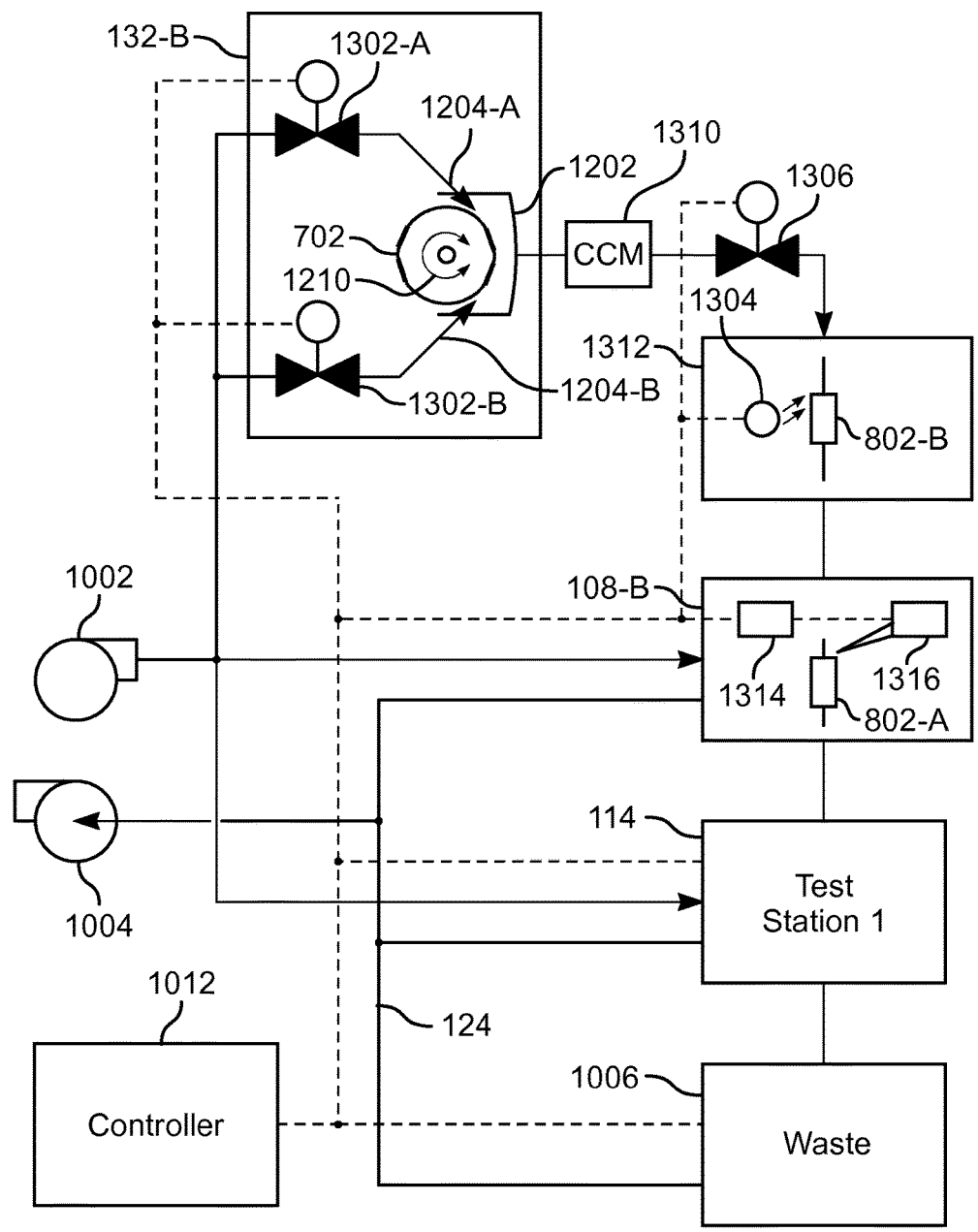
FIG. 13 is a simplified piping and instrumentation diagram of a sampling system with the embodiment of the sub-sampling mechanism shown in FIG. 12.

FIG. 13 illustrates a simplified piping and instrumentation diagram of a sampling system 100 with another embodiment of a sub-sampling mechanism 132-B. The illustrated sub-sampling mechanism 132-B employs the extraction drum 702 illustrated in FIGS. 11 & 12. Only a single drum 702 is illustrated. For the primary sample carrier 104-B illustrated in FIG. 6, a pair of drums 702 are used with the drums 702 side-by-side. In various embodiments, multiple sets of drums 702 are used based on the number of sub-sampler stations 150 in the cotton acquisition and tracking system 100.

A cotton containment mechanism (CCM) 1310 is located in the vacuum tubes downstream from the sub-sampling mechanism 132-B. The CCM 1310 prevents oversized masses of cotton fibers from flowing to the downstream components. In one embodiment, the CCM 1310 is a manual mechanism that detects a clump or oversized mass and allows for an operator to remove the clump or oversized mass. In another embodiment, the CCM 1310 is an automated mechanism that removes the clump or oversized mass without operator intervention.

Figure 18:
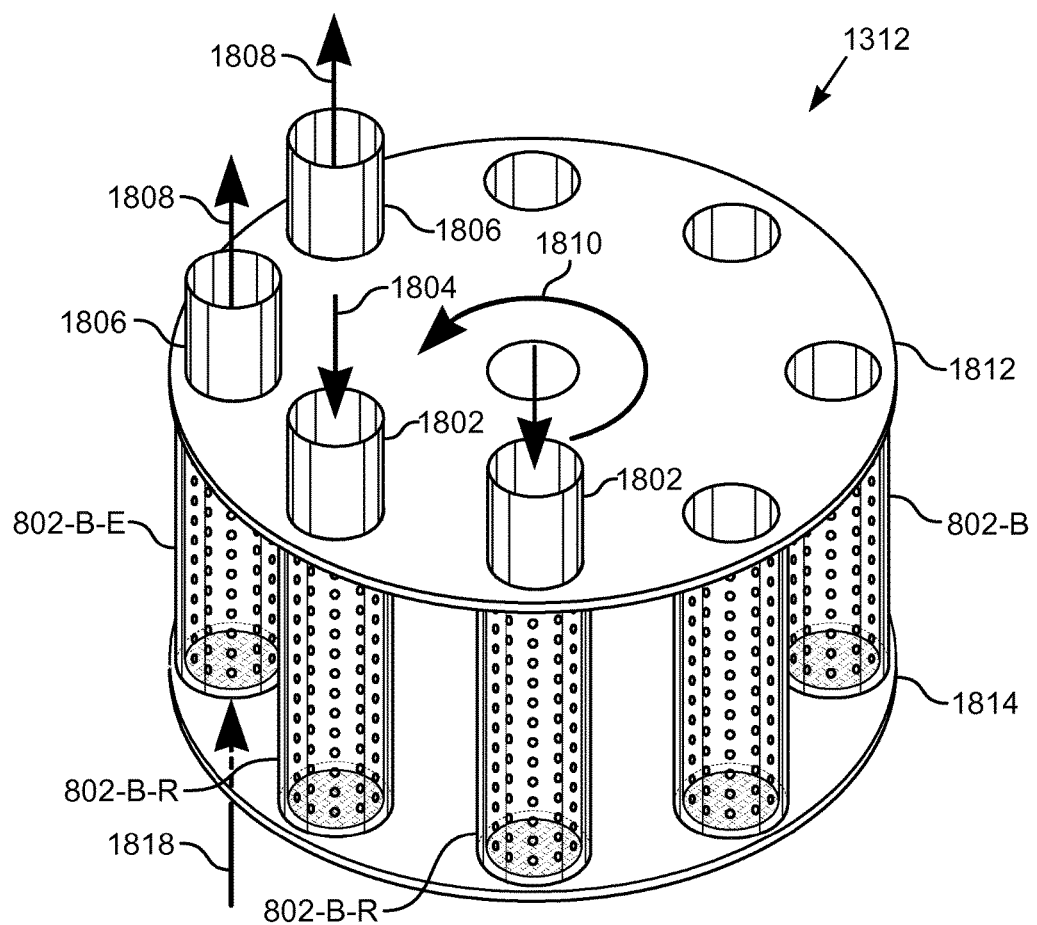
FIG. 18 is a perspective view of one embodiment of an indexer using the embodiment of the sub-sample carrier shown in FIG. 9.

The outlet of the cotton containment mechanism 1310 is directed to an indexer 1310, which provides sub-samples 102-SS to the sub-sample staging carousel 108-B. The indexer 1312 includes a plurality of sub-sample carriers 802-B, such as is shown in FIGS. 9 and 18. The illustrated embodiment shows an optical sensor 1304 that detects the presence of sufficient fibers for a sub-sample 102-SS. In various embodiments the sensor 1304 can measure various parameters, such as differential pressure, that indicate when sufficient fibers have been collected in the sub-sample carrier 802-B.

The outlet of the indexer 1310 is directed to a sub-sample staging carousel 108-B. The staging carousel 108-B stores sub-samples 102-SS in sub-sample carriers 802-A until such time that they are needed by the test station 114. Each sub-sample 102-SS in the carousel 108-B is associated with an identification device 1314. In one embodiment, the identification device 1314 is a writeable RFID that stores the sample identification code associated with the sub-sample 102-SS. The sub-samples 102-SS are loaded into empty sub-sample carriers 802-A and expelled from loaded sub-sample carriers 802-A by a combination of a rotary storage unit similar to that of the indexer 1312 and a swing arm 1316 that connects the pneumatic tubing to a selected sub-sample carrier 802-A. In operation, when receiving a sub-sample 102-SS, the carousel 108-B moves to an empty sub-sample carrier 802-A, thereby connecting the pneumatic system to the sub-sample carrier 802-A, which receives the sub-sample 102-SS. The carousel 108-B also writes the sample identification code to the identification device 1314. After receiving the sub-samples 102-SS the carousel 108-A rotates to move the newly loaded carriers 802-A away from the pneumatic tubing that delivered the sub-samples 102-SS and positions empty sub-sample carriers 802-A to receive the next sub-samples 102-SS. In this way the loaded carriers 802-A are positioned for the swing arm 1316 to extract the sub-samples 102-SS without requiring the carousel 108-B to move.

When a sample is to be removed, the swing arm 1316 moves to an full or loaded sub-sample carrier 802-A, thereby connecting the pneumatic system to the selected sub-sample carrier 802-A, which will allow the sub-sample 102-SS to be expelled from the carrier 802-A and the swing arm 1316 reads the sample identification code from the identification device 1314. In this way the controller 1012 keeps track of the samples being tested.

In one embodiment the indexer 1312 accommodates four pairs of sub-samples 102-SS. The staging carousel 108-B accommodates thirty-six pairs of sub-samples 102-SS. In this way, the staging device 108-B accommodates sufficient sub-samples 102-SS to provide test samples to the test station 114 in the event the sub-sampler 150 is interrupted, such as by a temporary slowdown or stoppage. Likewise, the staging device 108-B has sufficient capacity to accommodate storing sub-samples 102-SS in the event testing is interrupted. The staging device 108-B acts as a buffer for other system components.

The pneumatic system 124 includes an air pump 1002 that supplies conditioned air to the sub-sampling mechanism 132-B, the sub-sample staging device 108-A, 108-B, and test station one 114. The conditioned air from the air pump 1002 is directed toward the portion of the system 100 where the sub-sample 102-SS passes. The air is conditioned to maintain a specified temperature and relative humidity to condition the sub-samples 102-SS.

The pneumatic system 124 also includes a vacuum pump 1004 connected to the sub-sample staging device 108-A, 108-B, test station one 114, and the waste device 1006. The vacuum pump 1004 is selectively connected to various pipes and equipment to pull the fibers or the sub-sample 102-SS from one location to another within the pneumatic system 124. For example, the vacuum from the vacuum pump 1004 is used to pull the fibers from the extraction drum 702-A, through the three-way valve 714-A, and to the staging device 108, where the sub-sample 102-SS is held until test station one 114 is ready to test the sub-sample 102-SS.

A controller 1012 is connected to the sub-sampling mechanism 132-B, the valve 1306, the sub-sampling staging device 108, test station one 114, and the waste device 1006. The sensor 1304 monitors the sub-sample carrier 802-B to determine if the sub-sample 102-SS is within weight limits. The controller 1012 monitors the optical sensor 1304 and controls the sub-sampling mechanism 132-B and valves 1306 to collect more fibers until the desired volume or mass of the sub-sample 102-SS is obtained. The controller 1012 monitors test station one 114 and initiates the removal of a tested sub-sample 102-SS and the transfer of the next sub-sample 102-SS to be tested from the staging device 108. For example, the controller 1012 operates various valves in the pneumatic system 124 to pull the desired sub-sample 102-SS from the staging device 108 to test station one 114.

The sub-sampling mechanism 132-B includes an extraction drum 702 with a shroud 1202 to collect the extracted fibers, a pair of jet assemblies 1204-A, 1204-B, and valves 1302-A, 1302-B supplying pressurized air to corresponding assemblies 1204-A, 1204-B.

Figure 14:
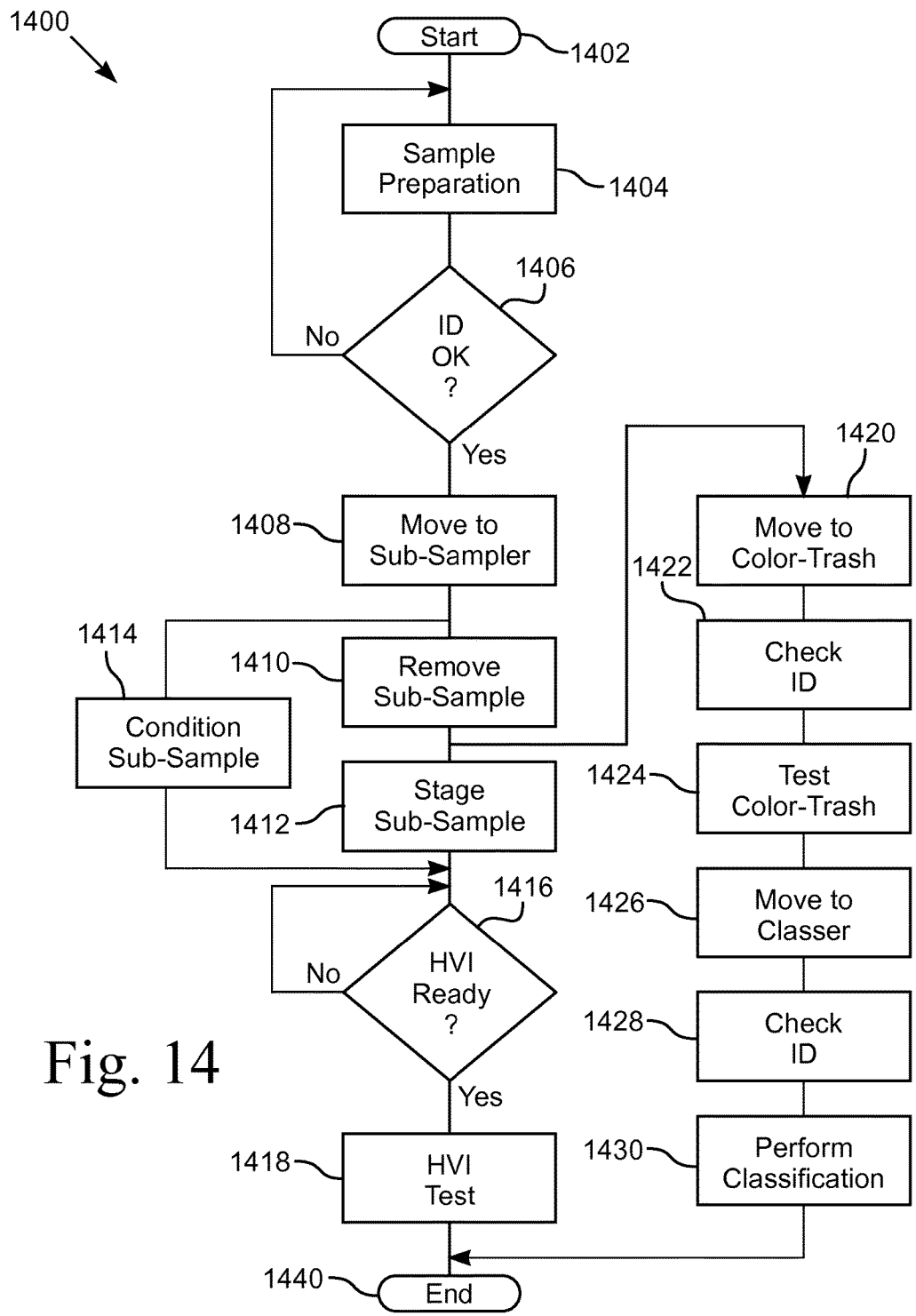
FIG. 14 is a flow diagram of one embodiment of the steps performed on a cotton sample moving through the sampling system.

FIG. 14 illustrates a flow diagram of one embodiment of the process 1400 performed on a cotton sample 102 moving through the sampling system 100. It is to be understood that the process 1400 is performed multiple times with the steps offset to accommodate the empty carriers 104 and the loaded primary sample carriers 104' moving through the sampling system 100 sequentially.

At the start 1402, the step of sample preparation 1404 is performed. The loading station 120 includes a stop on the conveyor 106 for the empty primary sample carriers 104 from the classer station 118. The production assistant 140 loads a primary bale sample 102 and a bale tag 404 into a primary sample carrier 104. The next step 1406 is to check the identifying tags on the loaded primary sample carrier 104' with the scanner 128 at the loading station 120. In one embodiment, the carrier has two identical tags 402 that uniquely identify the carrier 104. The bale tag 404 uniquely identifies the bale sample 102 to be tested and is attached to the carrier 104 by the production assistant 140. In one embodiment, the carrier tags 402 and the bale tag 404 contain bar codes that are optically read by the scanner 128. If all three tags 402, 404 are readable, the loaded primary sample carrier 104' moves to the next step 1408. If not, the carrier 104' does not move and the production assistant 140 must resolve the error by performing the sample preparation step 1404 again. In another embodiment, the bale tag 404 is not secured to the loaded primary sample carrier 104', but instead is used by the production assistant 140 to associate the bale tag 404 with the carrier tags 402 on the carrier 104 containing the sample 102. In such an embodiment, the code associated with the bale tag 404 is written to a radio frequency identification (RFID) tag 402 attached to the carrier 104.

After the identification verification step 1406 is successfully performed, the next step 1408 is to move the loaded primary sample carrier 104' to the sub-sampler station 150. The next step 1410 is to remove the sub-sample 102-SS from the primary sample 102.

After removing the sub-sample 102-SS, the next step is to stage the sub-sample 102-SS for later testing at test station one 114, for example, by testing with a high volume instrument (HVI). In one embodiment, the sub-sample 102-SS is staged at the sub-sampling distribution module 108-A, where the sub-samples 102-SS are stored until they are moved to test station one 114, In another embodiment, the sub-sample 102-SS is staged at the sub-sample staging carousel 108-B until test station one 114 is ready to test the sub-sample 102-SS.

While the sub-sample 108-B is being removed 1410 and staged 1412, the step 1414 of conditioning the sub-sample is performed. In this way, the volume of conditioning air 126 is minimized because only the sub-sample 102-SS is conditioned, not the entire primary sample 102. Additionally, the sub-sample 102-SS is stored in the staging device 108 for a time sufficient to ensure that the sub-sample 102-SS is conditioned.

After the sub-sample 102-SS is staged, the next step 1416 is to determine if the test station 1114 is ready to test a sample. If test station one 114 is ready, the next step 1418 is to perform the test at test station one 114. In one embodiment the step 1418 of performing the test includes discarding the sub-sample 102-SS at the end of testing. In one such embodiment, the tested sub-sample 102-SS is transferred through the pneumatic system 124 to a waste device 1006.

After the step 1410 of removing the sub-sample 102-SS, the next step 1420 is to move the primary sample 102 to test station two 116. At the test station two 116 the step 1022 of checking the identification tags 402, 404 is performed. After the identification is checked 1022, the step 1024 of testing is performed, for example, the color/trash test is performed. In one embodiment, the testing step 1424 is performed by the test station two operator 146 and includes performing the Cotton Micronaire test.

In another embodiment, the step 1424 of testing the color/trash is performed in conjunction with the step 1418 of the HVI test. In such an embodiment, after step 1412 of staging the sub-sample 102-SS, the loaded primary sample carrier 104' is moved to a specific color/trash station 116 associated with an HVI 114 that is available. After the step 1422 identifying the primary sample 102 identification, the associated sub-sample 102-SS is transferred to the HVI 114 for testing 1418. The color/trash station operator 146 proceeds with step 1424 by imaging the primary sample 102 while the HVI 114 performs the Cotton Micronaire test.

After the step 1424 of testing the color/trash, the step 1426 of moving the primary sample 102 to test station three 118 is performed. At test station three 118 the step 1428 of checking the identification tags 402, 404 is performed. After the identification is checked 1428, the step 1430 of performing the classification of the sample 102 is performed. In one embodiment, the classifying step 1430 is performed by the classer station operator 148 who enters the grade value and determines if the sample is being called for Specials, Studies, or Check-Lots. If called, the classer station operator 148 sets the associated primary sample 102 with the bale tag 404 aside for the other, called processes. If not called, the classer station operator 148 disposes of the primary sample 102 down a reclamation conveyor and the empty primary sample carrier 104 is returned to the loading station 120 for the next sample 102.

In one embodiment, the steps 1420, 1422, 1424 related to testing at test station two 116 are performed after the steps 1426, 1428, 1430 related to performing the classification.

After the step 1418 of performing the HVI test and the step 1430 of performing the classification are completed, the process for testing the sample 102 is ended 1440.

One embodiment of the cotton acquisition and tracking system 100 integrates an automated imaging system that eliminates the need for a separate color/trash station 116. The automated imaging system including high resolution cameras and related analytical algorithms. In various such embodiments, the imaging system is positioned within the cotton acquisition and tracking system 100 at any of a number of different locations. Referring to FIG. 14, in one embodiment, the automated imaging system is employed prior to step 1408 of moving the sample 102 to the sub-sampler. In another embodiment, the automated imaging system is positioned at the color/trash station 116 and used as part of step 1424 of testing color/trash.

One such embodiment of the automated imaging system has the primary sample carrier 104 positioned within the imaging system, and, after the identifying tags 402, 404 have been verified, the cameras automatically move into position above and below each half of the primary sample carrier 104 to capture two images of each half of the primary sample. The captured images and calculated data are stored and then paired with the test data from the HVI that performs the classing tests (step 1430) on the representative sub-samples. Once the test data from both operations has been paired and verified for sample integrity, the primary sample carrier 104 moves to either the sub-sampler (step 1408) or to the classer (step 1426), depending upon placement of the imaging system.

Figure 15:
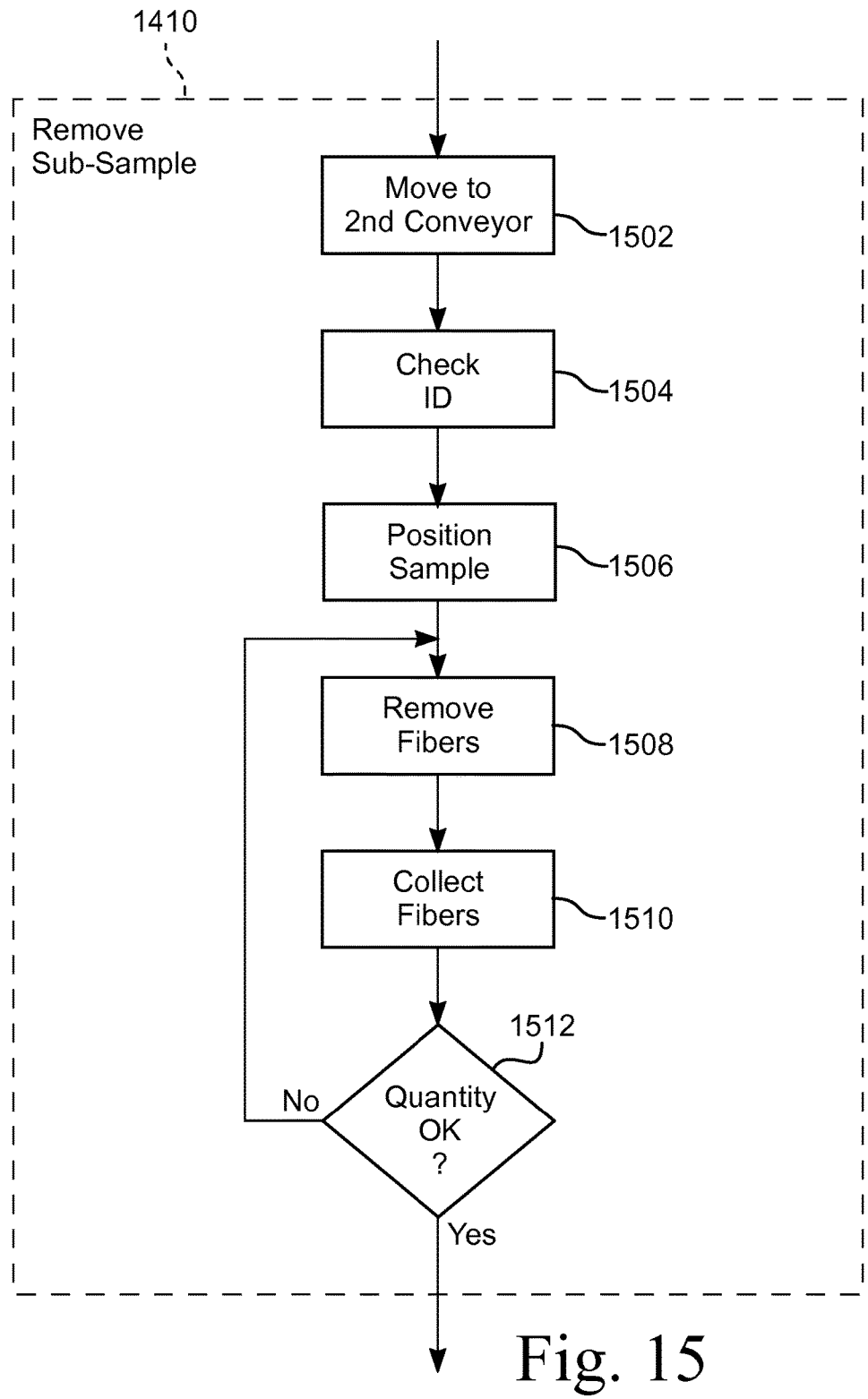
FIG. 15 is a flow diagram of one embodiment of the steps for removing the sub-sample.

FIG. 15 illustrates a flow diagram of one embodiment of the steps for removing the sub-sample 1410. At the sub-sampler station 150, the step 1410 of removing the sub-sample includes the step 1502 of moving the loaded primary sample carrier 104' from the main conveyor 106 to a second conveyor 130 and the step 1504 of checking the identity of the sample 102 in the primary sample carrier 104. The identity is checked, in one embodiment, by the scanner 128 that reads the tags 402, 404 on the sample carrier 104. Either of these two steps 1502, 1504 can be performed initially or simultaneously.

The next step 1506 is to position the sample on the second conveyor 130 such that the sub-sampling plate 204 of the primary sample carrier 104, 104' is positioned proximate the sub-sampling mechanism 132. This step 1506 includes pressing the sample 102 in the carrier 104, 104' against the sub-sampling plate or wall 204.

In one embodiment, the step 1506 of positioning the sample includes moving the filled primary sample carrier 104' to a stop adjacent the extraction drums 702. The filled primary sample carrier 104' is elevated from the conveyor 130 to align the windows 602 with the operating surface of the extraction drums 702. With the filled primary sample carrier 104' in position, a sample feed mechanism 1220 above each half of the sample 102 is lowered 1224. The sample feed mechanism 1220 includes a plurality of needles or picks 1222 that penetrate the cotton sample 102. The sample feed mechanism 1220 is operated by a pneumatic cylinder. A pressure sensor connected to the cylinder determines when the sample feed plate fully engages the sample 102 and provides a signal to stop the downward movement of the sample feed mechanism 1220. The sample feed mechanism 1220 is then moved horizontally 1226 to feed the sample 102 through the window 602 in the carrier 104-B. An optical sensor detects when the sample 602 protrudes outside the window 602 in the carrier 104-B and stops feeding the sample 102. The sample feed mechanism 1220 continues to feed the sample 102 as the extraction drum 702 extracts fibers from the sample 102.

After the positioning step 1506, the next step 1508 is to remove the fibers from the primary sample 102. In one embodiment, the fiber removing step 1508 is performed by the sub-sampling mechanism 132 picking fibers from the portion of the sample 102 protruding from the holes 214 in the sub-sampling plate 204. In another embodiment, the fiber removing step 1508 is performed by the sub-sampling mechanism 132 carding fibers from the portion of the sample 102 protruding from the holes 214 in the sub-sampling plate 204. For the embodiment where the fiber removing step 1508 is performed by carding, a extraction drum 702 moves relative to the primary sample 102.

The fibers are doffed via a vacuum from the pneumatic system 124. The next step 1510 is to collect the fibers in the sub-sample carrier 802. The pneumatic system 124 pulls the fibers from the sub-sampling mechanism 132 to the sub-sample carrier 802, where the quantity of the fibers making the sub-sample 102-SS is determined. In various embodiments, the quantity of fibers making the sub-sample 102-SS is based on weight, mass, and/or volume.

The step 1512 of determining if the quantity is correct is performed after the step of collecting fibers 1510. In one embodiment, the differential pressure across the fibers collected in the sub-sample carrier 802-A is measured by a differential pressure sensor 1008. If the differential pressure is lower than a preset limit, the measurement indicates that the collected fibers are not sufficient to meet the minimum quantity requirements. In another embodiment, the step 1512 of determining the quantity is implemented by measuring the height of the fibers in the sub-sample carrier 802-B using an optical sensor 1304.

If the collected fibers do not meet the quantity requirements as determined in step 1512, the step 1508 of removing fibers is repeated. If the collected fibers meet the quantity requirements as determined in step 1512, the step 1410 of removing the sub-sample 102-SS is completed and the process 1400 moves to the next step 1412 of staging the sub-sample 102-SS.

Figure 16:
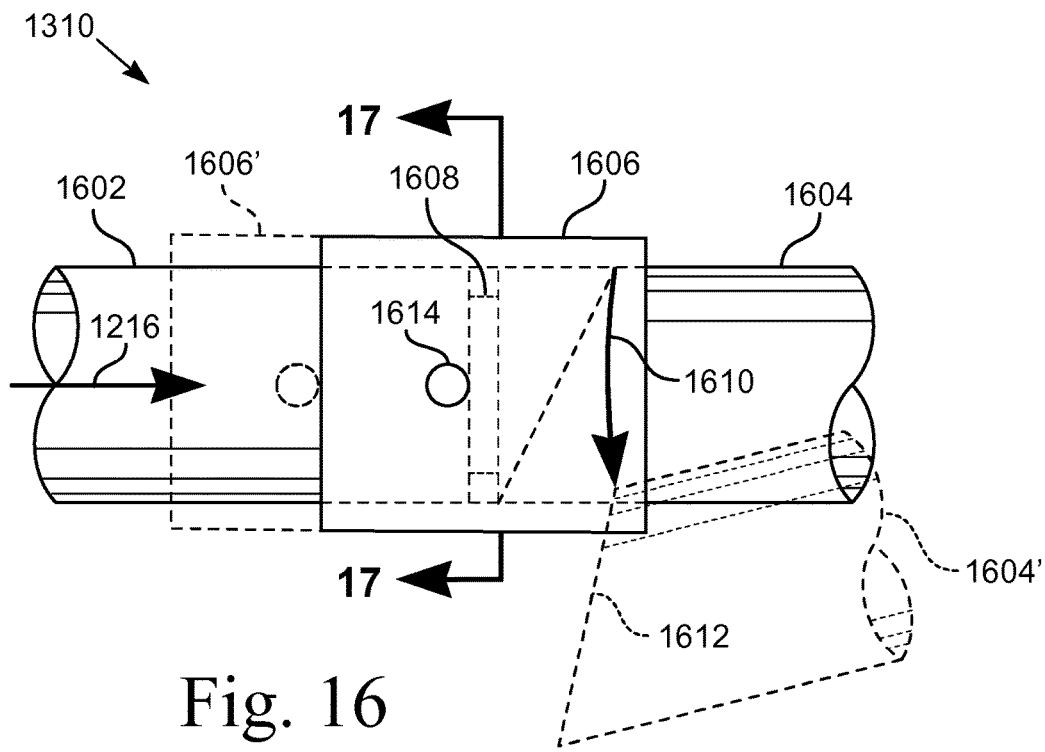
FIG. 16 is a partial side view of one embodiment of a cotton containment mechanism.
Figure 17:
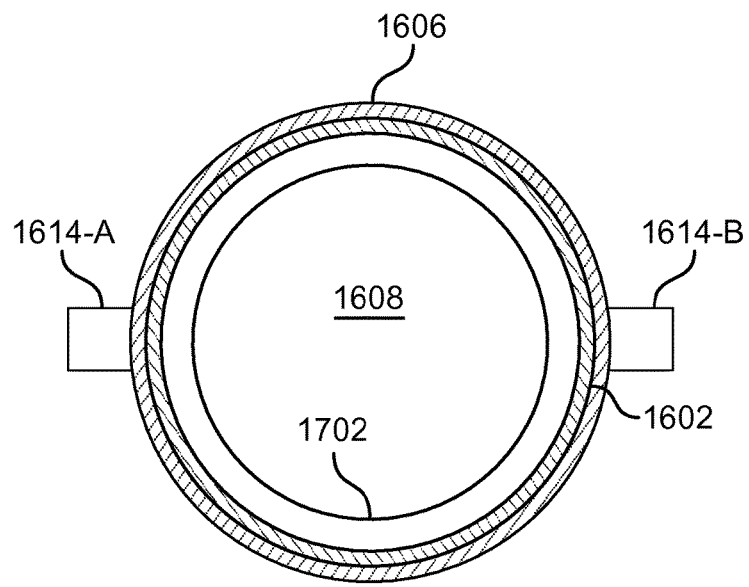
FIG. 17 is a cross-sectional view of the embodiment of the cotton containment mechanism shown in FIG. 16.

FIG. 16 illustrates a partial side view of one embodiment of a cotton containment mechanism (CCM) 1310. FIG. 17 illustrates a cross-sectional view of the embodiment of the cotton containment mechanism 1310 shown in FIG. 16.

During cotton acquisition, oversized clumps of cotton occasionally are removed from the primary sample and enter the vacuum air stream 1216. Some clumps are so large that they cause clogs in downstream components such as diverter valves, indexer tubes, and staging tubes. Oversized clumps often adversely affect sample mass range.

The cotton containment mechanism 1310 receives extracted fibers from a flow stream 1216 moving through the inlet tube 1602. The distal end of the inlet tube 1602 has a restrictor or orifice plate 1702 with a central opening or orifice 1608. The orifice 1608 is sized to capture oversized clumps so that they do not travel further into the system. The diameter of the orifice 1608 is dependent upon the flow rate and the size of clump desired to be stopped. The outlet tube 1604 mates with the distal end of the inlet tube 1602. The two tubes 1602, 1604 have an end 1612 cut at an oblique angle such that when the outlet tube 1604 pivots downward 1610 the outlet tube 1604' clears the distal end of the inlet tube 1602. Attached to the distal end of the inlet tube 1602 and overlapping the distal end is a sleeve or collar 1606. The sleeve 1606 conforms to the outer surface of the inlet tube 1602 and ensures alignment of the inlet and outlet tubes 1602, 1604 when the tubes 1602, 1604 are in a throughflow configuration. With the outlet tube 1604' in the pivoted downward 1610 position, the cotton containment mechanism 1310 is in the clump removal configuration because the clump caught by the orifice 1608 is accessible for removal from the distal end of the inlet tube 1602. Before the cotton containment mechanism 1310 leaves the throughflow configuration, the flow 1216 through the tubes 1602, 1604 is stopped, for example, by closing the valve 1306.

In the illustrated embodiment, the collar 1606 is a cylindrical tube that slides along the inlet and outlet tubes 1602, 1604. In the throughflow configuration the collar 1606 is positioned over the joined ends 1612 of the tubes 1602, 1604. In this way the collar 1606 ensures that the tubes 1602, 1604 are aligned and are sealed. To separate the tubes 1602, 1604, the collar 1606' is moved axially away from the joined ends 1612 such that the outlet tube 1604 is pivotable or movable 1610 such that outlet tube 1604' is out of the way and allows access to the distal end of the inlet tube 1602.

The cotton containment mechanism 1310 includes a restrictor plate 1702, optical or differential pressure sensors 1614, and separable containment chamber 1602. Restrictor plates 1702 are sized to prevent targeted mass ranges of clumps from entering the airstream downstream of the plate 1702. The sensors 1614 detect a blockage and trigger a clearing action and confirm the blockage has been cleared before the sub-sample process can be resumed. In one embodiment, the sensors 1614 include a light source 1614-A and a light sensor 1614-B. The sensors 1614 are attached to the sleeve 1606 and move with the sleeve 1606. The sensors 1614 rely upon the translucent material of the inlet tube 1602 for the optical signal from the sensors 1614 to be responsive to any buildup of fibers indicating a clump is present at the restrictor plate 1702. When a clump collects at the orifice 1608, the light from the source 1614-A is blocked by the clump and the light sensor 1614-B detects the absence of light, thereby sensing the presence of a clump needing removal. In another embodiment, the sensors 1614 are differential pressure sensors that include an upstream pressure sensor 1614-A and a downstream pressure sensor 1614-B. A differential pressure of a specified magnitude between the two sensors 1614-A, 1614-B indicates the presence of a clump. In such an embodiment the sensors 1614 mate with an opening in the inlet tube 1602 when the sleeve 1606 is in the throughflow configuration. In another such embodiment, the differential pressure sensors 1614 tap into the inlet and outlet tubes 1602, 1604 away from the sleeve 1606, thereby avoiding having the sensors 1614 move with the sleeve 1606. The containment chamber consist of a tube 1602 with a diagonally cut distal end. The containment chamber 1602 and the outlet tube 1604 are held together with the overlapping sleeve or collar 1606.

In one embodiment, the cotton containment mechanism 1310 is a manual mechanism that detects a clump or oversized mass and allows for an operator to remove the clump or oversized mass. With the inlet tube 1602 held statically in position, the sleeve 1606 is moved axially away from the tube end 1612, thereby allowing the outlet tube 1604 to pivot in a direction 1610 away from the inlet tube 1602 and allowing the two tubes 1602, 1604 to be separated. With the two tubes 1602, 1604 separated and the cotton containment mechanism 1310 in the clump removal configuration, the clump is exposed and is manually removed.

In another embodiment, the cotton containment mechanism 1310 is an automated mechanism that removes the clump or oversized mass without operator intervention. In one such embodiment, the automated cotton containment mechanism 1310 includes an actuator that slides the sleeve 1606 away from the tube end 1612 and moves the outlet tube 1604 into the clump removal configuration and a clump picker then removes the clump. In another such embodiment, the automated cotton containment mechanism 1310 includes a shuttle between the inlet and outlet tubes 1602, 1604. The orifice 1608 is in the shuttle. Upon detection of a clump in the CCM 1310, the shuttle is slide away from the tubes 1602, 1604 and a reverse air flow is used to blow the clump away from the orifice 1608 for disposal. The cleared orifice 1610 is then returned to position and the CCM 1310 is returned to the throughflow configuration.

FIG. 18 illustrates a perspective view of one embodiment of an indexer 1312 using the embodiment of the sub-sample carrier 802-B shown in FIG. 9. The indexer 1312 includes a plurality of sub-sample carriers 802-B positioned between a pair of plates 1812, 1814. The indexer 1312 rotates in a direction 1810 that positions each of the sub-sample carriers 802-B in alignment with a pair of collection inlets 1802 and a pair of extraction outlets 1806. Because the primary sample 102 is divided into halves with each half providing a sub-sample 102-SS, a pair of sub-sample carriers 802-B are associated with each primary sample 102. In the illustrated embodiment, the indexer 1312 is configured to accommodate four pairs of sub-samples 102-SS from four primary samples 102.

The top plate 1812 connects to a pair of collection inlets 1802 that has an air flow direction 1804 into a pair of receiving sub-sample carriers 802-B-R. The flow direction 1804 is such that the air stream 1804 flows into the opening in the top plate 1812, through the receiving sub-sample carrier 802-B-R, and out the opening in the bottom plate 1814. The fibers flowing in the air stream are stopped by the mesh 804 in the carrier 802-B-R. When a sub-sample 102-SS has been collected in the carrier 802-B-R, the sub-sample 102-SS is conditioned by the continuous flow of conditioned air through the carrier 802-B. After the pair of sub-samples 102-SS are collected, the indexer 1312 rotates to position a pair of empty sub-sample carriers 802-B in line with the collection inlets 1802.

The top plate 1812 connects to a pair of extraction outlets 1806 that has an air flow direction 1818 into the bottom of a pair of extraction sub-sample carriers 802-B-E. The flow direction 1818, 1808 is such that the sub-sample collected and stored in the sub-sample carrier 802-B-E is pushed out of the carrier 802-B-E by a positive air pressure applied through openings in the bottom plate 1814. The blown out sub-samples 102-SS are then routed to a staging device 108. Each carrier 802-B includes a one-way valve 906 that prevents the air flow 1818 from entering the space between the cylinders 806, 902. Instead, the positive air pressure is directed axially 1818, 1808 through the mesh 804 and carrier 802-B-E. After the sub-samples 102-SS have been extracted from the carrier 802-B-E, the indexer 1312 rotates to position another pair of sub-sample carriers 802-B in line with the extraction outlets 1806.

The illustrated embodiment of the indexer 1312 has eight sub-sample carriers 802-B. To facilitate efficiency the collection and extraction operations occur in parallel. In one such embodiment, the indexer 1312 has a pair of collection inlets 1802 and extraction outlets 1806. In this way the throughput of the indexer 1312 is increased by double. In such an embodiment, the indexer 1312 rotates 1810 in increments of two, that is, each carrier 802-B moves two slots over when the indexer 1312 is rotated.

Figure 19:
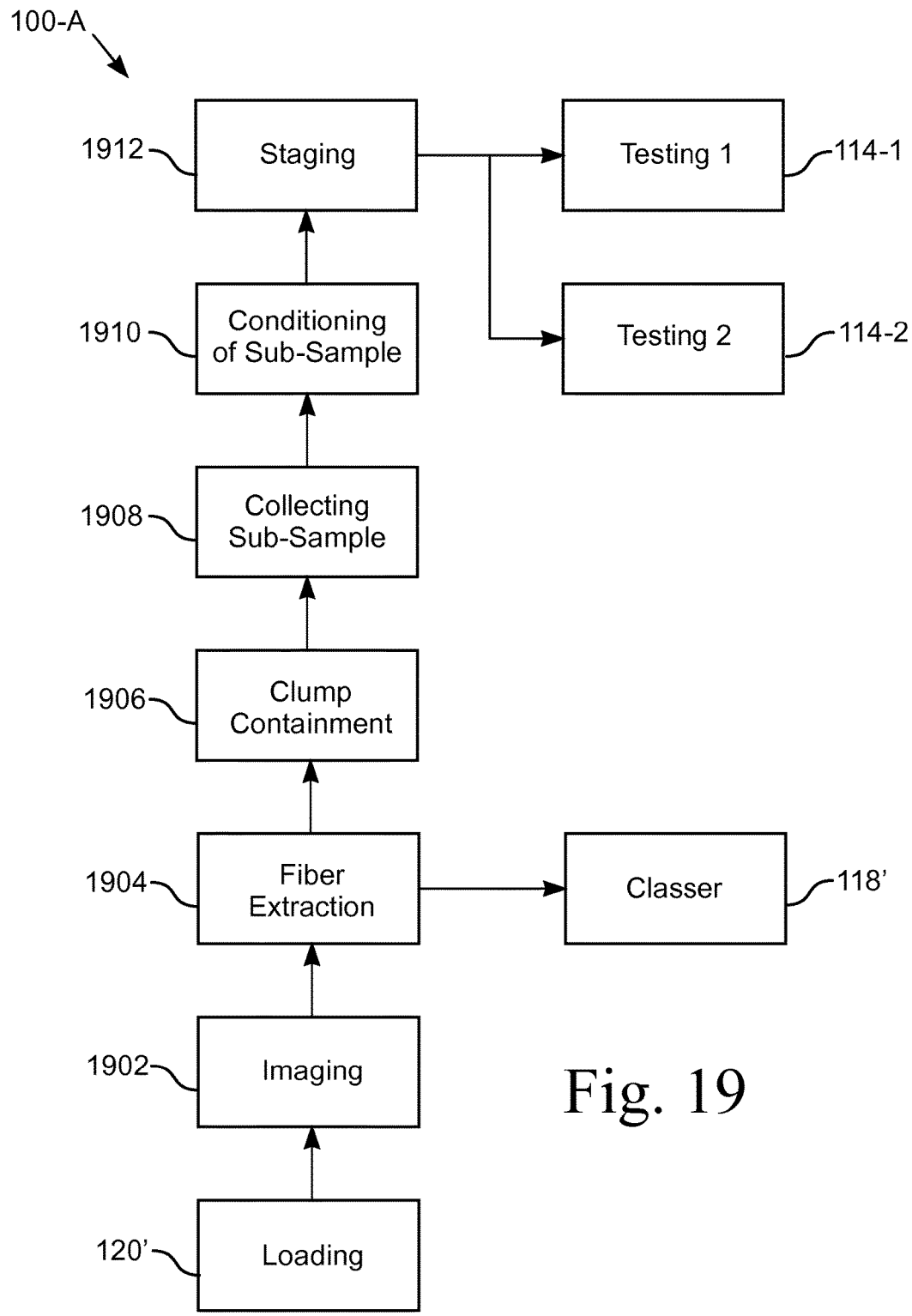
FIG. 19 is a block diagram of another embodiment of a cotton acquisition and tracking system.

FIG. 19 illustrates a block diagram showing the functions of one embodiment of a cotton acquisition and tracking system 100-A. The illustrated embodiment includes a loading station 120', such as the auto-loading station previously described. The loading station 120' transports the primary sample 102 to an imaging station 1902, such as an automated imaging system that eliminates the need for a separate color/trash station 116. The primary sample 102 is then transported to a device that performs the function of fiber extraction 1904 from the primary sample 102. The primary sample 102 is then transported to the classer station 118'. In one embodiment the classer station 118' is the final arbiter of the validity of the testing process. Generally, the classer station 118' examines the primary sample 102 after all the other testing is completed.

The fiber extraction 1904 pulls fibers from the primary sample 102. The fibers from the fiber extraction device 1904 pass through a clump containment 1906, and then are collected 1908 into a sub-sample 102-SS before the sub-sample 102-SS is conditioned 1910. The sub-samples 102-SS are sent to the staging device 1912, where the sub-samples 102-SS are kept until the testing stations 114-1, 114-2 are ready to accept a sub-sample 102-SS. The system 100-A is configurable to accommodate multiple testing stations 114-1, 114-2, based on the throughput of the sub-sampler 150'.

In the illustrated embodiment the primary sample 102 moves from loading 120', to imaging 1902, to fiber extraction 1904, and to the classer 118', after which the primary sample 102 is discarded. In one embodiment the primary sample 102 is minimally handled and a primary sample carrier 104 is not needed to transport the samples 102. The sub-samples 102-SS move as fibers from the device that performs the fiber extraction 1904 function to clump containment 1906 where oversized groups of fibers are restricted. The fibers are then are collected 1908 into a sub-sample 102-SS. The sub-samples 102-SS are conditioned 1910 and then move to staging 1912, where the sub-samples 102-SS are distributed to one of multiple testing stations 114-1, 114-2.

In one embodiment, the fiber extraction 1904 and clump containment 1906 functions are embodied in a sub-sampler 132 and the collecting 1908 and conditioning 1910 functions are embodied in an indexer 1312. In various embodiments the collecting 1908 and conditioning 1910 functions are embodied in a sub-sampler 132 or a staging device 108.

The cotton acquisition and tracking system 100 includes various functions. The function of collecting fibers for a sub-sample is implemented, in one embodiment, by the sub-sampler mechanism 132-B that includes a drum 702 with carding pucks 722 and an air puffer system 1202, 1204, 1206 that removes the fibers from the pucks 722 for collection downstream. The function of acquiring a sub-sample 102-SS is implemented, in one embodiment, by the sub-sampling mechanism 132 that pulls fibers from the primary sample 102 and collects those fibers in the indexer 1312 as a sub-sample 102-SS.

The function of conditioning the sub-sample 102-SS is implemented, in one embodiment, by the indexer 1312, which collects the fibers in a sub-sample carrier 802-B while routing conditioned air through the carrier 802-B and the fibers. The sub-sample carrier 802-B is a double-walled chamber that routes air axially and radially through the fibers of the sub-sample 102-SS. In one embodiment the conditioned air is ambient air that has been conditioned to have a specified temperature and humidity. In another embodiment the conditioned air is from a closed system that supplies conditioned air to the pneumatic system.

The function of oversized clump control is implemented, in one embodiment, by the cotton containment mechanism 1310 that includes a restrictor plate 1702 with an orifice sized to collect clumps of fibers that exceed a specified mass or size.

The function of feeding the primary sample 102 to the sub-sampler drum 702 is implemented, in one embodiment, by the sample feed mechanism 1220, that includes a plate with picks 1222 that move along two axes 1224, 1226. One axis 1224 allows the mechanism 1220 to engage the primary sample 102 and the other axis 1226 allows the mechanism 1220 to move the sample 102 relative to the drum 702 for removal of fibers.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

What is claimed is:

1. An apparatus for acquiring, conditioning, and testing cotton sub-samples, said apparatus comprising:
   a loading station that receives and identifies a primary sample of fibrous material where a primary sample identification code corresponds to an identification code of a source of said primary sample;
   a sub-sampler that extracts a sub-sample from said primary sample, said sub-sampler including a sample feed mechanism and a drum, said sample feed mechanism advancing said primary sample against said drum, said drum including a plurality of pucks configured to grab a plurality of fibers from said primary sample that are collected to form a sub-sample, said pucks including carding wire configured to engage said primary sample when said drum rotates, said drum reciprocating with said plurality of pucks moving relative to said primary sample, said sub-sampler further including a shroud around a portion of said drum, said shroud having an outlet at a negative pressure relative to an ambient pressure outside said shroud, said shroud configured to draw air from around said drum through said outlet of said shroud thereby capturing said plurality of fibers extracted from said primary sample;
a conditioning system that routes conditioned air through said sub-sample; and
a pneumatic routing system configured to transport said sub-sample to a test station.

2. The apparatus of claim 1 further including a plurality of air jets positioned to direct an air stream toward said plurality of pucks and toward said outlet of said shroud, and said air stream being a series of high pressure air blasts timed to strike said plurality of pucks to aid in blowing said plurality of fibers off said plurality of pucks.

3. The apparatus of claim 1 further including a sample feed mechanism that includes a plurality of picks that move along a first axis and a second axis, said first axis being perpendicular to a plane defined by said primary sample, and said second axis being parallel to said plane of said primary sample and perpendicular to an axis of rotation of said drum, whereby said sample feed mechanism grasps said primary sample and feeds said primary sample towards said drum.

4. The apparatus of claim 1 wherein said sub-sampler includes a cotton containment mechanism to remove an oversized clump of cotton, said cotton containment mechanism includes a first tube with a restrictor plate, and said restrictor plate having an orifice sized to capture said oversized clump of cotton having a specified mass.

5. The apparatus of claim 1 further including an indexer, said indexer including a plurality of sub-sample carriers wherein one of said plurality of sub-sample carriers collects said plurality of fibers to form said sub-sample.

6. The apparatus of claim 5 wherein each one of said plurality of sub-sample carriers include a first cylinder having a distal end with a mesh sized to stop said plurality of fibers from passing completely through said first cylinder.

7. The apparatus of claim 5 wherein each one of said plurality of sub-sample carriers include a first cylinder inside a second cylinder with an air gap therebetween, said first cylinder having a distal end with a mesh sized to stop said plurality of fibers from passing completely through said first cylinder, and said first cylinder having a plurality of spaced openings along a sidewall of said first cylinder whereby an air stream entering a space between said first and second cylinders flows through said plurality of spaced openings into said first cylinder thereby conditioning said sub-sample.

8. The apparatus of claim 1 wherein said sub-sample is stored in a staging device until ready to be transported to said at least one test station, said staging device configured to expose said sub-sample to a conditioned environment, and said staging device including a plurality of sub-sample carriers each having a re-writeable identification device that identifies a corresponding sub-sample stored in one of said plurality of sub-sample carriers.

9. The apparatus of claim 1 further including a primary sample carrier, said primary sample carrier including a first compartment and a second compartment, said first and second compartments dimensioned and configured to receive a portion of said primary sample, said primary sample carrier including an identifier associated with an identification of said primary sample, and said primary sample carrier including at least one access port in each of said first and second compartments, and said at least one access port configured to allow said plurality of pucks to engage said primary sample.

10. An apparatus for acquiring, conditioning, and testing cotton sub-samples, said apparatus comprising:
a loading station that receives and identifies a primary sample of fibrous material where a primary sample identification code corresponds to an identification code of a source of said primary sample;
a sub-sampler that extracts a sub-sample from said primary sample, said sub-sampler configured to grab a plurality of fibers from said primary sample and introduce said plurality of fibers into an air stream;
an indexer receiving said air stream with said plurality of fibers from said sub-sampler, said indexer collecting said plurality of fibers into a sub-sample carrier to form a sub-sample, said sub-sample carrier including a first cylinder having a distal end with a mesh sized to stop said plurality of fibers from passing completely through said first cylinder, said sub-sample carrier includes a second cylinder with said first cylinder disposed inside said second cylinder with an air gap therebetween, and said first cylinder being permeable to air along a sidewall of said first cylinder whereby an air stream entering a space between said first and second cylinders flows through said sidewall into said first cylinder thereby conditioning said sub-sample, and said sub-sample carrier further includes a one-way valve adjacent said mesh, said one-way valve preventing air from flowing from outside said first cylinder adjacent said mesh and between said first and second cylinders whereby a puff of air introduced into said sub-sample carrier to remove said sub-sample from said first cylinder is isolated to said first cylinder;
a conditioning system that routes conditioned air through said sub-sample in said first cylinder; and
a pneumatic routing system configured to transport said sub-sample to a test station.

11. The apparatus of claim 10 wherein said sub-sample carrier further includes a second cylinder with said first cylinder disposed inside said second cylinder with an air gap therebetween, and said first cylinder having a plurality of openings in a sidewall of said first cylinder whereby an air stream entering a space between said first and second cylinders flows through said sidewall into said first cylinder thereby conditioning said sub-sample.

12. The apparatus of claim 10 wherein said primary sample includes a pair of primary sample halves, said sub-sampler configured to provide two streams of said plurality of fibers with each stream from one of said pair of primary sample halves, and said indexer having a pair of said sub-sample carriers each configured to receive one of said two streams of said plurality of fibers whereby a pair of sub-samples is collected from said primary sample.

* * * * *